US012678484B2

(12) United States Patent
Balasubramanian et al.

(10) Patent No.: US 12,678,484 B2
(45) Date of Patent: Jul. 14, 2026

(54) METHODS OF TREATMENT WITH PEGFILGRASTIM AND ROMIPLOSTIM

(71) Applicant: Amgen Inc., Thousand Oaks, CA (US)

(72) Inventors: Ganesh Balasubramanian, Lexington, MA (US); Deborah I. Bunin, Thousand Oaks, CA (US); Polly Y. Chang, Thousand Oaks, CA (US); Simon Authier, Laval (CA); Sameer V. Doshi, Thousand Oaks, CA (US); James Bakke, Menlo Park, CA (US); Janet Gahagen, Menlo Park, CA (US); Karen Wong, Laval (CA); Mark Fielden, Thousand Oaks, CA (US)

( * ) Notice: Subject to any disclaimer, the term of this patent is extended or adjusted under 35 U.S.C. 154(b) by 34 days.

(21) Appl. No.: 16/979,493

(22) PCT Filed: Mar. 11, 2019

(86) PCT No.: PCT/US2019/021687
§ 371 (c)(1),
(2) Date: Sep. 9, 2020

(87) PCT Pub. No.: WO2019/173839
PCT Pub. Date: Sep. 12, 2019

(65) Prior Publication Data
US 2021/0015901 A1     Jan. 21, 2021

Related U.S. Application Data

(60) Provisional application No. 62/734,899, filed on Sep. 21, 2018, provisional application No. 62/657,594, filed on Apr. 13, 2018, provisional application No. 62/641,224, filed on Mar. 9, 2018.

(51) Int. Cl.
*A61K 38/19* (2006.01)
*A61P 7/04* (2006.01)
(52) U.S. Cl.
CPC .......... *A61K 38/196* (2013.01); *A61K 38/193* (2013.01); *A61P 7/04* (2018.01)
(58) Field of Classification Search
None
See application file for complete search history.

(56) References Cited

FOREIGN PATENT DOCUMENTS

| JP | 2014-097958 A | 5/2014 |
| WO | 2014/077358 A1 | 5/2014 |

OTHER PUBLICATIONS

Yamaguchi et al. (Blood(2015) 126(23):2390).*
Staff et al. (https://globalbiodefense.com/2015/12/03/pegfilgrastim-neulasta-acute-radiation-syndrome/ Dec. 3, 2015).*
Hankey et al. ("Pegfilgrastim improves survival of lethally irradiated nonhuman primates" Radiation research , 183(6):643-655).*
Voloshin et al. ("Romiplostim after autologous peripheral blood progenitor cell transplantation: results of a pilot study" vol. 18 (2) supplement S316, Feb. 2012).*
Nplate dose calculator (<https://www.medicines.org.uk/emc/rmm/270/Document>Sep. 13, 2015).*
Centene (file:///C:/Users/tmartinez/Downloads/CP.PHAR.296%20Pegfilgrastim%20(1).pdf Apr. 15, 2016).*
Amirian et al., "Spontaneous Bleed in a Patient with Thrombocytopenia Due to Multi-System Langerhan's Histiocytosis," *J. Med. Cases* 6(8): 376-377 (2015).
Anonymous, "Interventional Study in Adults With Immune Thrombocytopenia Purpura ITP) Receiving Romiplostim," History of Changes for Study: NCT01143038 dated. Feb. 7, 2017, ClinicalTrials. gov, retrieved from the internet: <URL: https://clinicaltrials.gov/ct2/history/NCT01143038?A=36&B=36&C-merged#StudyPageTo.p>.
Anonymous, "Trial to Compare the Efficacy and Safety of Pegfilgrastim Biosimilar in Subjects With High Risk Stage Breast Cancer Receiving Chemotherapy," Identifier: NCT02768714 dated Sep. 15, 2017, ClinicalTrials.gov, retrieved from the internet: <URL: https://clinicaltrials.gov/ct2/show/NCT02768714?term-NCT02768714&draw=2&rank=1>.
Bosch-Vilaseca et al., "Usefulness of thrombopoietin receptor agonists for persistent clinically relevant thrombocytopenia after allogeneic stem cell transplantation," *European Journal of Haematology* 101(3): 407-414 (2018).
Farese et al., "Combined Administration of Recombinant Human Megakaryocyte Growth and Development Factor and Granulocyte Colony-stimulating Factor Enhances Multilineage Hematopoietic Reconstitution in Nonhuman Primates after Radiation-induced Marrow Aplasia," *J Clin Invest.* 97(9):2145-2151 (1996).
Grossmann et al., "Synergistic Effects of Thrombopoietin and Granulocyte Colony-Stimulating Factor on Neutrophil Recovery in Myelosuppressed Mice," *Blood* 88(9):3363-3370 (1996).

(Continued)

*Primary Examiner* — Tara L Martinez
(74) *Attorney, Agent, or Firm* — Amgen Inc.

(57) ABSTRACT

The present invention concerns methods comprising co-administration of pegfilgrastim and romiplostim for treatment of diseases and conditions characterized by low neutrophil levels (neutropenia) and/or low platelet levels (thrombocytopenia). The present invention concerns an enhanced effect on neutrophil levels and on platelet levels resulting from co-administration of pegfilgrastim and romiplostim. The present invention further concerns a method of treating a patient who has been exposed to radiation, which comprises administering romiplostim at a dose of about 1 to about 10 µg/kg. The invention further concerns such methods wherein a single dose of romiplostim is administered to the patient and wherein romiplostim is administered about 24 hours or less after the radiation exposure. The invention further concerns treatment with romiplostim and pegfilgrastim for radiation exposure. Such methods relate to treatment of acute radiation syndrome and treatment to counteract the effects of radiation therapy and other sources of radiation exposure.

5 Claims, 25 Drawing Sheets

(56) References Cited

OTHER PUBLICATIONS

Hankey et al., "Pegfilgrastim Improves Survival of Lethally Irradiated Nonhuman Primates," *Radiation Research* 183(6):643-655 (2015).

Hirouchi et al., "Mitigative Effects of a Combination of Multiple Pharmaceutical Drugs on the Survival of Mice Exposed to Lethal Ionizing Radiation," *Current Pharmaceutical Biotechnology* 17(2):190-199 (2016).

Inagaki et al., "Prognostic impact of the mean platelet volume/platelet count ratio in terms of survival in advanced non-small cell lung cancer," *Lung Cancer* 83(1):97-101 (2014).

International Search Report in PCT Application No. PCT/US2019/021687 dated Aug. 13, 2019.

Kiang et al., "Combined Therapy of Pegylated G-CSF and A1xn4100TPO Improves Survival and Mitigates Acute Radiation Syndrome after Whole-Body Ionizing Irradiation Alone and Followed by Wound Trauma," *Radiation Research* 188:476-490 (2017).

Kohler et al., "G-CSF-mediated thrombopoietin release triggers neutrophil motility and mobilization from bone marrow via induction of Cxcr2 ligands," *Blood* 117(16):4349-4357 (2011).

Kovtonyuk et al., "Enhanced thrombopoietin but not G-CSF receptor stimulation induces self-renewing hematopoietic stem cell divisions in vivo," *Blood* 127(25): 3175-3179 (2016).

Ku et al., "Thrombopoietin, the Ligand for the Mpl Receptor, Synergizes with Steel Factor and Other Early Acting Cytokines in Supporting Proliferation of Primitive Hematopoietic Progenitors of Mice," *Blood* 87(11):4544-4551 (1996).

Kumagai et al., "Prognostic significance of preoperative mean platelet volume in resected non-small-cell lung cancer," *Mol Clin Oncol.* 3(1):197-201 (2015).

Neelis et al., "The Efficacy of Single-Dose Administration of Thrombopoietin with Coadministration of Either Granulocyte/Macrophage or Granulocyte Colony-Stimulating Factor in Myelosuppressed Rhesus Monkeys," *Blood* 90(7):2565-2573 (1997).

Neelis et al., "Simultaneous administration of TPO and G-CSF after cytoreductive treatment of rhesus monkeys prevents thrombocytopenia, accelerates platelet and red cell reconstitution, alleviates neutropenia, and promotes the recovery of immature bone marrow cells," *Exp Hematol.* 25(10):1084-1093 (1997).

Sitnicka et al., "The Effect of Thrombopoietin on the Proliferation and Differentiation of Murine Hematopoietic Stem Cells," *Blood* 87(12):4998-5005 (1996).

Stickney et al., "5-androstenediol improves survival in clinically unsupported rhesus monkeys with radiation-induced myelosuppression," *Int Immunopharmacol.* 7(4):500-505 (2007).

Thompson et al., "Platelet Size and Age Determine Platelet Function Independently," *Blood* 63(6):1372-1375 (1984).

Vandraas et al., "Persistent bone marrow depression following short-term treatment with temozolomide," *BMJ Case Reports*, vol. 2016, DOI: 10.1136/bcr-2016-215797, 2016.

Voloshin et al. "Romiplostim after Autologous Peripheral Blood Progenitor Cell Transplantation: Results of a Pilot Study," *Biology of Blood and Marrow Transplantation* 18(2):S316 (2012).

Wong et al., "Effects of Romiplostim and Pegfilgastim on Acute Radiation-Induced Thrombocytopenia and Neutropenia in the Non-Human Primate," *Clinical Pharmacology & Therapeutics* 105(suppl 1):S115 (2019).

Written Opinion in PCT Application No. PCT/US2019/021687 dated Aug. 13, 2019.

Yamaguchi et al., "Thrombopoietin-Mimetic Romiplostim Confers the Complete Survival Rate to Mice Exposed to Lethal Ionizing Radiation," *Blood* 126(23):2390 (2015).

* cited by examiner

FIG. 2

| Group[a] | TBI Dose (cGy) | Romiplostim Dose (μg/kg) | Sex | $T_{max}$ (hr) | $C_{max}$ (ng/ml) Mean | SE | $t_{1/2}$ (hr) | $AUC_{last}$ (hr·ng/ml) Mean | SE | $AUC_{inf}$ (hr·ng/ml) |
|---|---|---|---|---|---|---|---|---|---|---|
| 1 | 0 | 30 | Male | 12 | 7 | 3.2 | NC[b] | 92 | 33 | NC |
| 1 | 0 | 30 | Female | 24 | 7 | 1.1 | NC | 387 | 48 | NC |
| 3 | 680 | 30 | Male | 12 | 6 | 0.5 | 24.3 | 228 | 17 | 248 |
| 3 | 680 | 30 | Female | 24 | 5 | 0.3 | NC | 219 | 13 | NC |
| 4 | 680 | 300 | Male | 4 | 201 | 58.3 | 29.9 | 8912 | 456 | 10089 |
| 4 | 680 | 300 | Female | 12 | 184 | 21.0 | 25.8 | 6903 | 364 | 7583 |

Platelet count

- ● Grp1 Saline + TBI
- ■ Grp2 Nplate 3 μg/kg + TBI
- ▲ Grp3 Nplate 30 μg/kg + TBI
- ◆ Grp4 Nplate 300 μg/kg + TBI
- ○ Grp5 untreated controls White Blood Cell Count <table>
<tr><td>●</td><td>Grp1 Saline + TBI</td></tr>
<tr><td>■</td><td>Grp2 Nplate 3 μg/kg + TBI</td></tr>
<tr><td>▲</td><td>Grp3 Nplate 30 μg/kg + TBI</td></tr>
<tr><td>♦</td><td>Grp4 Nplate 300 μg/kg + TBI</td></tr>
<tr><td>o</td><td>Grp5 untreated controls</td></tr>
</table>

Red Blood Cell Count

Neutrophil Cell Count

Reticulocyte Count

Kaplan-Meier Survival Analysis: 21 mice/sex/group

— Saline
— Nplate 3μg/kg
---- Nplate 10μg/kg
--- Nplate 30μg/kg
—— Nplate 100μg/kg Kaplan-Meier Survival Analysis: 21 mice/sex/group ——— Saline
——— 30µg/kg Romiplostim
—·—·— 300µg/kg Pegfilgrastim
— — — Both Survival Curves of a 45 Day Study in Male Group 1: Control
Group 2: RP (Day 1) 2.5 mg/kg
Group 3: RP (Day 1) 5 mg/kg
Group 4: PF (Day 1+8) 0.3 mg/kg
Group 5: RP (Day 1+8) 5mg/kg
Group 6: RP (Day 1) 5 mg/kg + PF (Day 1+8) 0.3 mg/kg Body Weight (kg)

Day

METHODS OF TREATMENT WITH PEGFILGRASTIM AND ROMIPLOSTIM

CROSS-REFERENCE TO RELATED APPLICATIONS

This application is a National Stage application under 35 U.S.C. § 371 of International Application No. PCT/US2019/021687, having an international filing date of Mar. 11, 2019, which claims the benefit of U.S. Provisional Patent Application No. 62/641,224, filed Mar. 9, 2018, and U.S. Provisional Patent Application No. 62/657,594, filed Apr. 13, 2018, and U.S. Provisional Patent Application No. 62/734,899, filed Sep. 21, 2018, and all of which are incorporated herein by reference in their entirety for all purposes.

ACKNOWLEDGEMENT OF GOVERNMENT SUPPORT

This invention was made with government support under HHSN272201500013I awarded by National Institutes of Health, National Institute of Allergy and Infectious Diseases, Department of Health and Human Services. The government has certain rights in the invention.

BACKGROUND OF THE INVENTION

Romiplostim (Nplate®) is a thrombopoiesis-stimulating peptibody that binds to the thrombopoietin receptor (TPO-R) on platelets and platelet precursors. Romiplostim binds to and activates TPO-R via a mechanism similar to that of endogenous TPO to stimulate growth and maturation of megakaryocytes, resulting in an increase in circulating platelets (PLT). Earlier publications documented the PK and PD of romiplostim in mice, non-human primates, and healthy and diseased humans. This led in 2008 to it being approved in the use and later in various regions of the world as a therapeutic for chronic primary immune thrombocytopenia purpura (ITP), an autoimmune disorder characterized by persistently low platelet counts. It is approved for use in adults in the United States for treatment of chronic ITP insufficiently responsive to corticosteroids, immunoglobulins, or splenectomy, and in Europe for those who have had a splenectomy and are refractory to other treatments or as second-line treatment in non-splenectomized patients for whom surgery is contraindicated. Romiplostim is administered at a starting dose of 1 μg/kg with weekly doses adjusted by 1 μg/kg to achieve and maintain a platelet count $\geq 50 \times 10^9$/L but no more than $400 \times 10^9$/L.

Pegfilgrastim (Neulasta®) is a form of the recombinant granulocyte colony stimulating factor (GCSF) analog filgrastim (Neupogen®) linked to monomethoxypolyethylene glycol. Pegfilgrastim thus mimics the activity of GCSF, which binds to and activates specific cell surface receptors, stimulating neutrophil progenitor proliferation and differentiation and selected neutrophil functions. The conjugation of the GCSF analog with a polyethylene glycol molecule significantly increases its therapeutic half-life. In the United States, pegfilgrastim is approved to decrease the incidence of infection manifested by febrile neutropenia in patients with non-myeloid malignancies receiving myelosuppressive anti-cancer drugs associated with a clinically significant incidence of febrile neutropenia. The recommended dosage of pegfilgrastim is a single subcutaneous injection of 6 mg administered once per chemotherapy cycle. Pegfilgrastim is also indicated to increase survival in patients acutely exposed to myelosuppressive doses of radiation. For this indication, the recommendation is for two doses, 6 mg each, administered subcutaneously one week apart.

A search of the medical and scientific literature failed to show any reported co-administration of pegfilgrastim and romiplostim. The literature did, however, include reports of co-administration of filgrastim and romiplostim.

Vandrass et al. report such co-administration to a patient who had received temozolomide, resulting in bone marrow failure. Vandraas et al. (2016), *BMJ Case Reports* 2016; 2016: bcr2016215797. These authors found only a transient increase in granulocyte levels, leading them to discontinue filgrastim after one month, and little effect on thrombocytes despite an increasing dosage of romiplostim, which they discontinued after two months of treatment.

Bosch-Vilaseca et al. report such co-administration in a retrospective study on the usefulness of thrombopoietin (TPO) agonists, eltrombopag and romiplostim, for persistent clinically relevant thrombocytopenia after allogeneic stem cell transplantation. Bosch-Vilaseca et al. (2018), *Eur. J. Hematol.* 101(3): 407-14. They identified as possible variables associated with higher response to TPO agonists age <40 years, presence of megakaryocytes in the bone marrow aspirate, and/or prior response to other hematopoietic growth factors. They found that response to TPO agonists (i.e., increased platelet levels) was documented in 6/13 patients having a response to filgrastim (i.e., increased white blood cell levels).

Amiriana et al. report such co-administration in treatment of a patient with mult-system organ involvement in Langerhan's cell histiocytosis. Amiriana et al. (2015), *J. Med. Cases* 6(8): 376-7. They report that the patient was given filgrastim and romiplostim to stimulate bone marrow production of leukocytes and platelets, finding that the leukocyte count responded while the platelet count did not.

Kovtonyuk et al. report co-administration of filgrastim and romiplostim in research on inducing hematopoietic stem cells (HSCs). Kovtonyuk et al. (2016), *Blood.* 127(25): 3175-3179. Based on in vivo high-resolution single HSC divisional tracking, they conclude that they demonstrated that clinically applied TPO receptor but not G-CSF receptor agonists drive HSCs into self-renewing divisions leading to quantitative expansion of functional HSC as defined by their in vivo serial multilineage and long-term repopulating potential. These results, they conclude, suggest that thrombopoietin mimetics might be applicable to expand HSCs in vivo and to sensitize thrombopoietin receptor-expressing HSCs to cell cycle-dependent cytotoxic agents.

An indication of interest for both pegfilgrastim and romiplostim is acute hematopoietic syndrome of acute radiation syndrome (HS-ARS). Rapid depletion of white blood cells, platelets and reticulocytes in HS-ARS results in infections, hemorrhages, and death. Given the possibility of radiological accidents and acts of terrorism and the severity of disease resulting from radiation exposure, there is a pressing need for the development and approval of effective medical countermeasures (MCM) for radiation syndromes. HS-ARS is characterized by neutropenia, thrombocytopenia, and anemia. To date, no medication has been shown to affect the platelet levels attendant to HS-ARS.

SUMMARY OF THE INVENTION

The present invention relates to methods comprising co-administration of pegfilgrastim and romiplostim for treatment of diseases and conditions characterized by low neutrophil levels (neutropenia) and/or low platelet levels (thrombocytopenia). The present invention concerns an enhanced effect on neutrophil levels and on platelet levels resulting from co-administration of pegfilgrastim and romiplostim. The method is hereby demonstrated in non-human primate studies of ARS, but such studies support treatment of other conditions characterized by low levels of platelets and/or neutrophils. The preferred doses in such co-administration are about 1-10 µg/kg romiplostim and about 6 mg pegfilgrastim for HS-ARS. The preferred dose frequency is two 6 mg doses of pegfilgrastim, one week apart. Other doses are suitable for other indications, including the doses approved by the US Food and Drug Administration for pegfilgrastim and romiplostim.

In accordance with the present invention is a process in which pegfilgrastim and romiplostim are administered wherein romiplostim is administered as follows:

a. administering an initial dose of 1 mcg/kg once weekly, and b. adjusting weekly doses by increments of 1 meg/kg to achieve and maintain a platelet count ≥50×10$^9$.

Further in accordance with the present invention is a process in which pegfilgrastim and romiplostim are administered wherein 6 mg of pegfilgrastim is administered. When the platelet level is affected by chemotherapy, romiplostim and pegfilgrastim are administered in which pegfilgrastim is preferably administered once per chemotherapy cycle, preferably at a dose of 6 mg.

Further in accordance with the present invention are methods of treatment for conditions characterized by low platelet levels or increased breakdown of platelets. Accordingly, the invention concerns methods of administering romiplostim and pegfilgrastim to a mammal wherein the mammal has been exposed to radiation (e.g., acute radiation syndrome, radiation therapy for cancer); has received or is receiving chemotherapy; or has a condition such as idiopathic thrombocytopenia purpura (ITP), viral infection, bacterial infection, thrombotic thrombocytopenia purpura, hemolytic uremic syndrome, or anemia (e.g., aplastic anemia).

Further in accordance with the present invention are methods of treating conditions characterized by low neutrophil levels or breakdown of neutrophils. Accordingly, the invention concerns methods of administering romiplostim and pegfilgrastim to a mammal wherein the mammal has been exposed to radiation (e.g., acute radiation syndrome, radiation therapy); has received or is receiving chemotherapy; or has a condition such as chronic idiopathic neutropenia, Kostmann's syndrome, leukemia, myelodysplastic syndrome, myelofibrosis, myelokathexis, vitamin deficiency, hepatitis A, hepatitis B, hepatitis C, HIV infection, AIDS, lyme disease, malaria, viral infection of the bone marrow, salmonella infection, sepsis, hypersplenism, or rheumatoid arthritis.

In accordance with the present invention, romiplostim is an effective medical countermeasure (MCM) for the treatment of HS-ARS and radiation exposure based on its ability to boost platelet production. In accordance with the present invention is a method of treating a patient who has been exposed to radiation, which comprises administering romiplostim. Further in accordance with the present invention is such a method wherein a single dose of romiplostim is administered to the patient. Further in accordance with the present invention are such methods wherein the patient so treated has acute radiation syndrome. Further in accordance with the present invention are such methods wherein the exposure to radiation is through radiation therapy as comprised in cancer treatment. Treatment of other sources of radiation exposure are also within the scope of this invention.

In the methods practiced in accordance with the present invention, male and female C57BL/6J mice were total body irradiated (TBI) with 680 cGy X-rays that reduce 30-day survival to 30% (LD$_{7/30}$). Romiplostim was administered subcutaneously (sc) with doses of 3, 30 or 100 µg/kg as a single dose or 30 µg/kg (for up to 5 doses) at ≥24 hours after TBI to assess survival benefit of the treatment. Pharmacokinetic (PK) and hematological parameters were also evaluated.

In the results from the foregoing methods, a single romiplostim dose (30 or 100 µg/kg) given 24 hours after TBI increased survival by about 40% in mouse studies. Multiple single daily dose of 30 µg/kg romiplostim given after TBI for up to 3 or 5 days were equally efficacious. Platelet levels reduced rapidly in romiplostim-treated TBI mice, reaching nadir on Day 8 before robust recovery. Conversely, PLT levels in vehicle-treated TBI mice reached nadir on about Day 10 and lagged before starting to recover. Kinetic profiles of other hematology parameters were similar between TBI romiplostim-treated and vehicle control mice. Peak serum levels of romiplostim in TBI mice occurred 4-24 hours (T$_{max}$) after injection with a t$_{1/2}$ of about 24 hours. C$_{max}$ values were at about 6 ng/ml after 30 µg/kg+/− TBI and about 200 ng/ml after 300 µg/kg. A 10-fold higher romiplostim dose increased the AUC$_{last}$ values by about 35-fold.

Among the conclusions drawn from the foregoing results are that single or multiple doses of romiplostim injection(s) in mice administered 24 hours after TBI increased survival and hastened PLT recovery. PK results+/−TBI showed that romiplostim is absorbed and efficiently distributed in mice.

Further in accordance with this invention is a method of treating acute radiation syndrome, which comprises administering romiplostim at a dose of about 1 to about 10 µg/kg.

Further in accordance with the present invention is a method of treating acute radiation syndrome comprising administration of romiplostim together with pegfilgrastim, which has a greater effect than either agent alone. The combination of both agents was associated with the lowest platelet and neutrophil nadirs compared to data on each agent alone in a study of non-human primates. The combination treatment also resulted in the earliest platelet and neutrophil recovery compared to each agent alone.

BRIEF DESCRIPTION OF THE FIGURES

FIG. 2 is a table showing romiplostim pharmacokinetics in irradiated vs. non-irradiated mice. Serum concentrations of romiplostim were <LLOQ in all samples in Group 2 (see Detailed Description of the Invention hereinafter), which received 600 cGy and 3 µg/kg of romiplostim. "NC" in the table refers to "not calculated" due to insufficient data points in the terminal phase for accurate calculation of values. For the values in the table, n=3/group/sex/time point.

FIGS. 1A, 1B and 2 show that (a) romiplostim was readily and efficiently absorbed after subcutaneous injection; (b) a similar pharmacokinetic (PK) profile with and without irradiation and in both sexes for 30 µg/kg; (c) T$_{max}$ was between 4-24 hours, T$_{1/2}$ about 24 hours; (d) C$_{max}$ and area under the curve (AUC) increased more than dose proportionality; (e) a 10-fold higher romiplostim dose increased the $C_{max}$ and $AUC_{last}$ exposure values by about 35-fold.

Figure 1A:
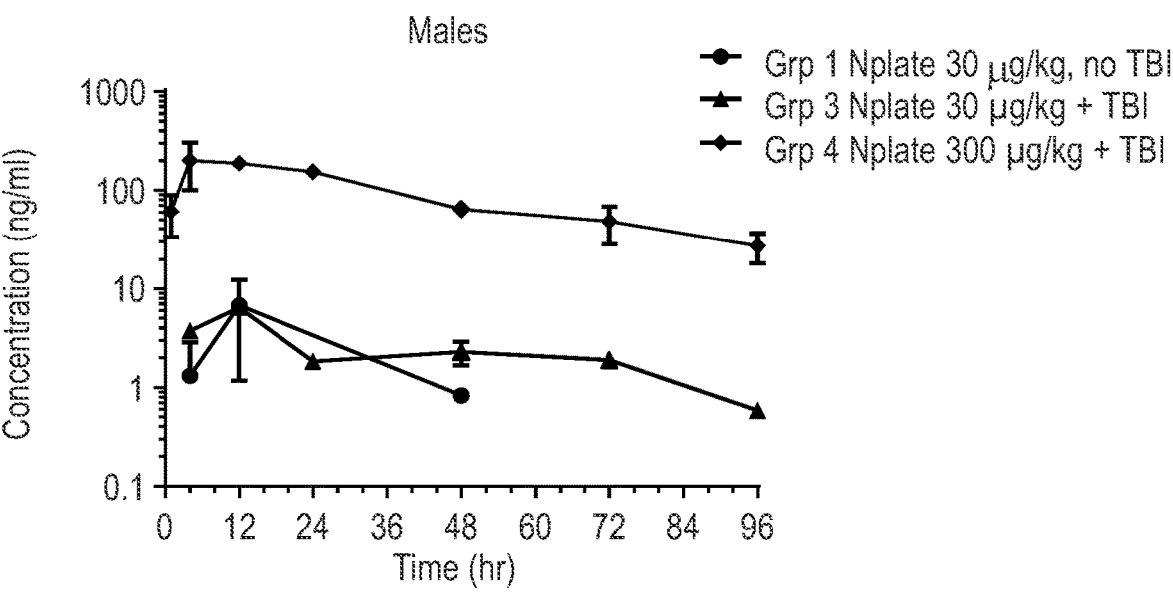
FIGS. 1A and 1B show serum concentrations of romiplostim after single subcutaneous doses 24-26 hours post-irradiation in male and female mice, respectively.
Figure 1B:
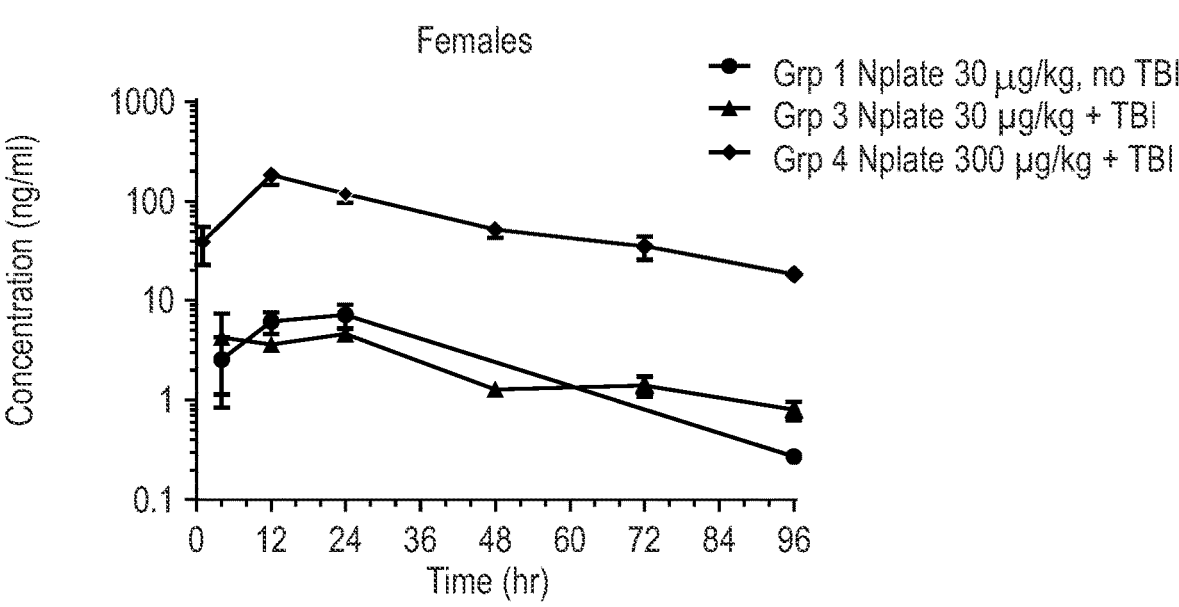
Figure 3A:
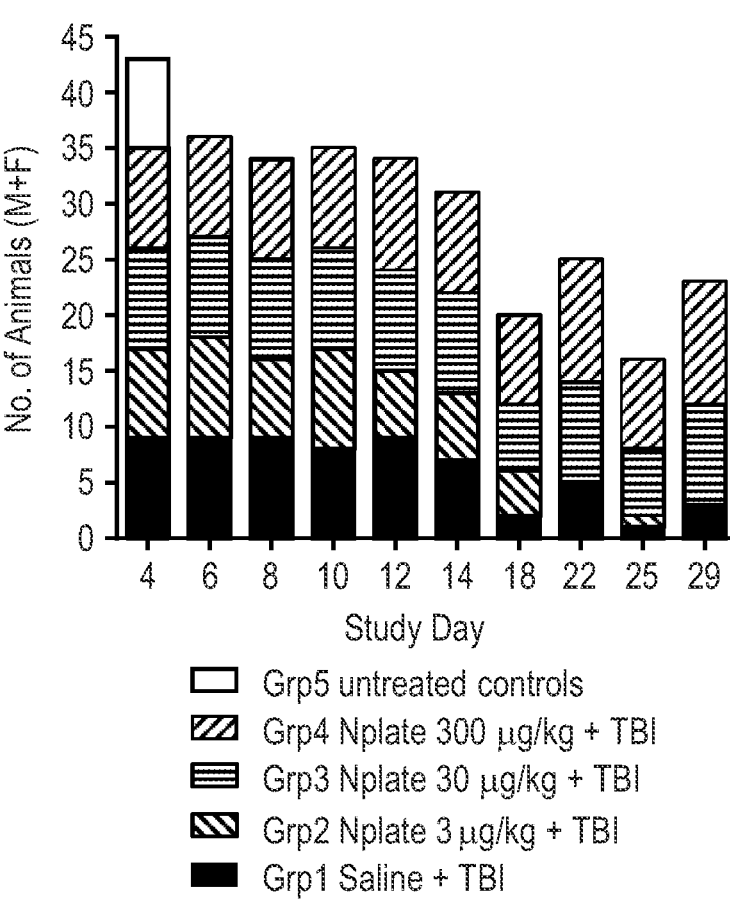
Figure 3B:
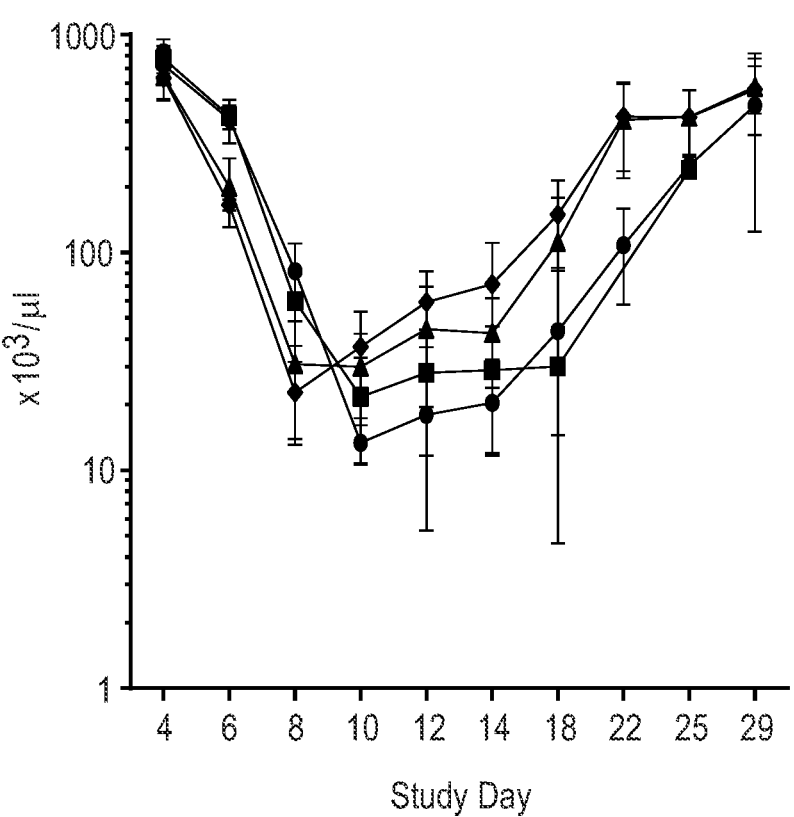
Figure 3C:
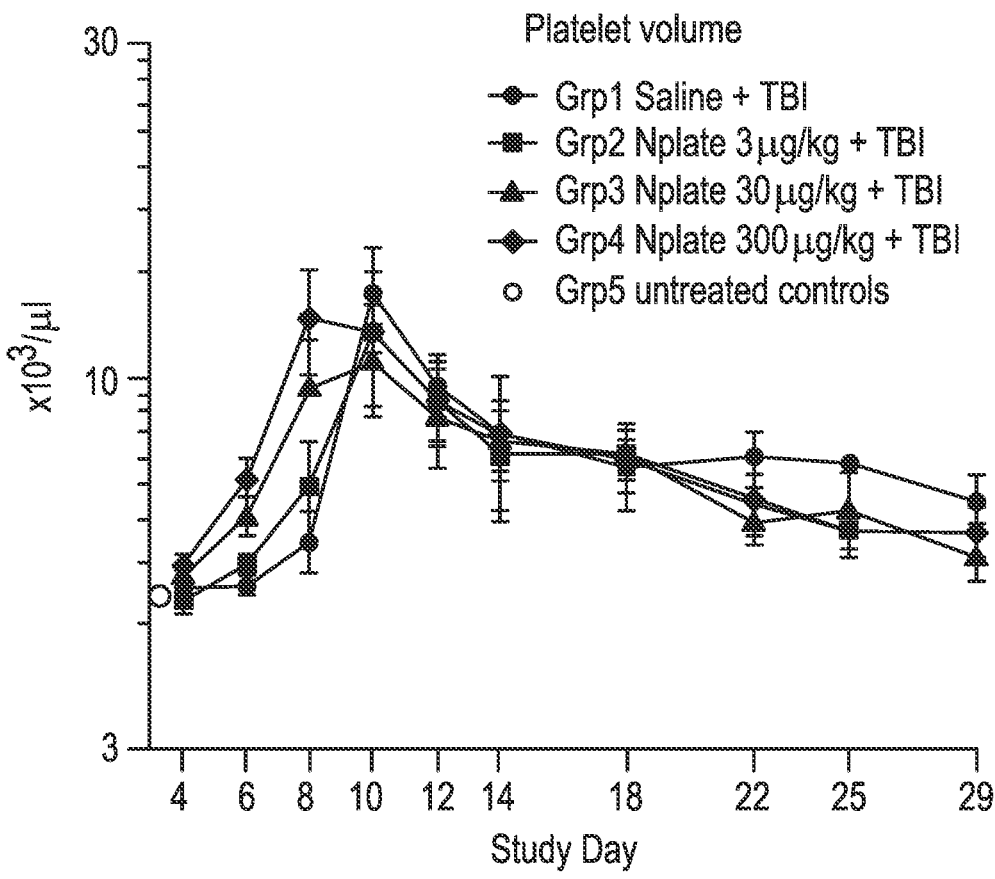

FIG. 3A-3C show romiplostim pharmacodynamics (PD) in irradiated vs. non-irradiated mice after a single dose. In FIG. 3A, the number of surviving, irradiated animals available for blood collection dropped drastically in vehicle controls (black) and low dose (blue) mice after Day 14. In FIG. 3B, platelet levels were approximately the same for all dose groups on Day 4. FIG. 3B shows that in the 30 and 300 μg/kg dose groups faster and less severe drop in platelet levels are seen after irradiation (nadir Day 8 vs. Day 10) vs. the saline and 3 μg/kg groups. Faster recovery to near baseline is seen in Day 22 vs. Day 29. In FIG. 3C, Platelet volume increased in mid- and high-dose groups on Days 6-8. This finding suggests a more rapid release of new platelets from the bone marrow after romiplostim administration in irradiated mice.

Figure 4A:
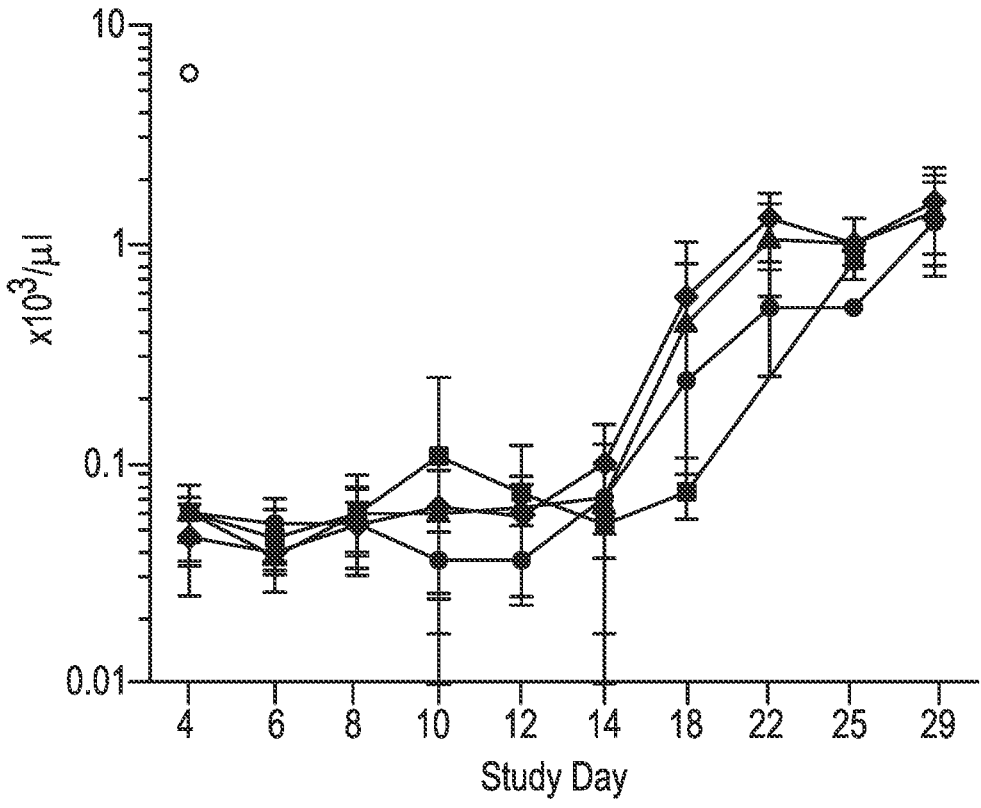
Figure 4B:
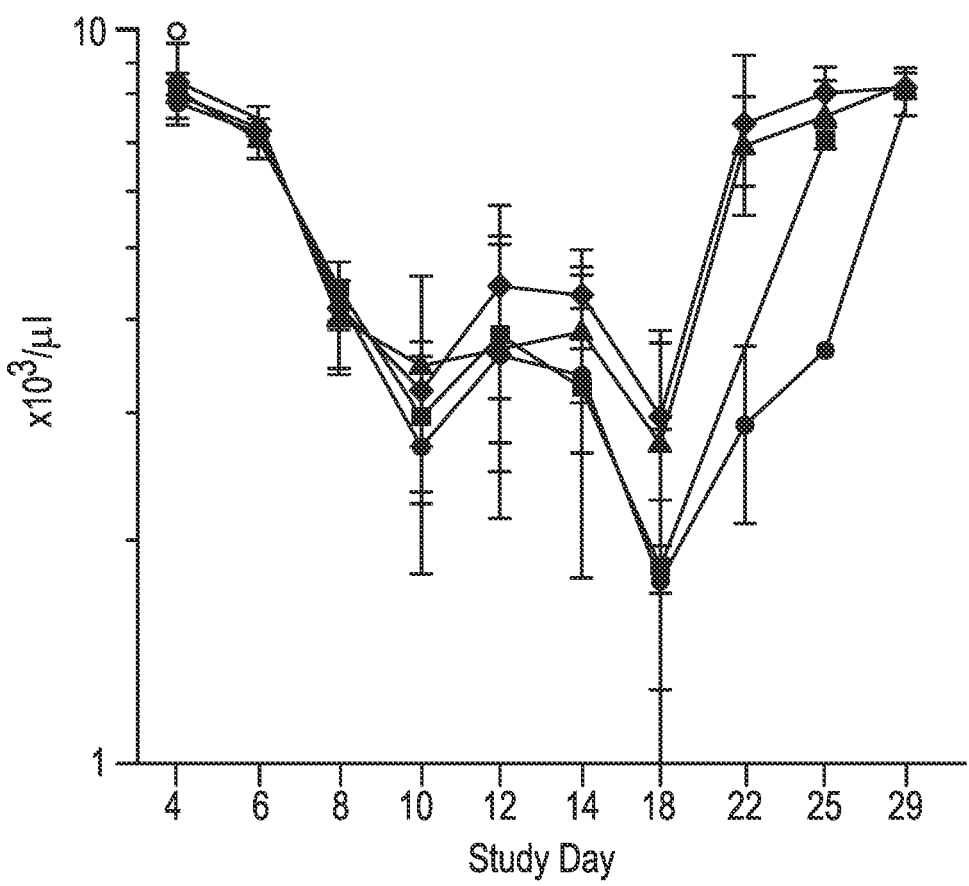
Figure 4C:
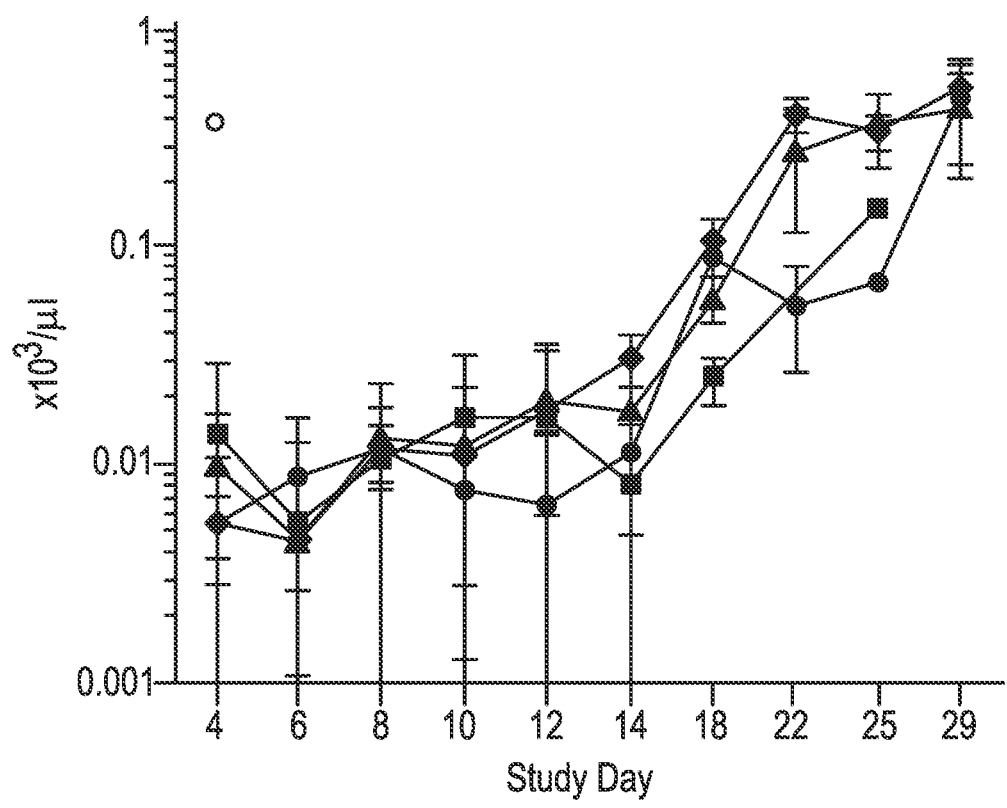
Figure 4D:
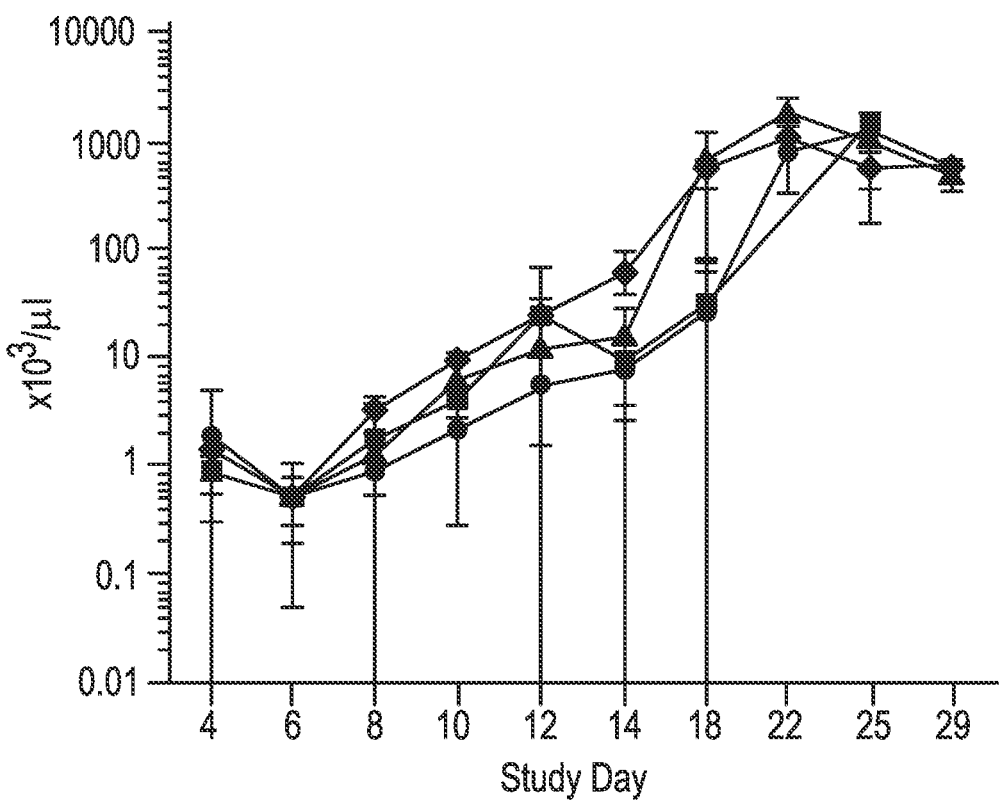

FIGS. 4A-4D show other major hematology parameters affected by radiation but not by romiplostim. The parameters shown are white blood cell count (FIG. 4A), red blood cell count (FIG. 4B), neutrophil cell count (FIG. 4C), and reticulocyte count (FIG. 4D).

Figure 5A:
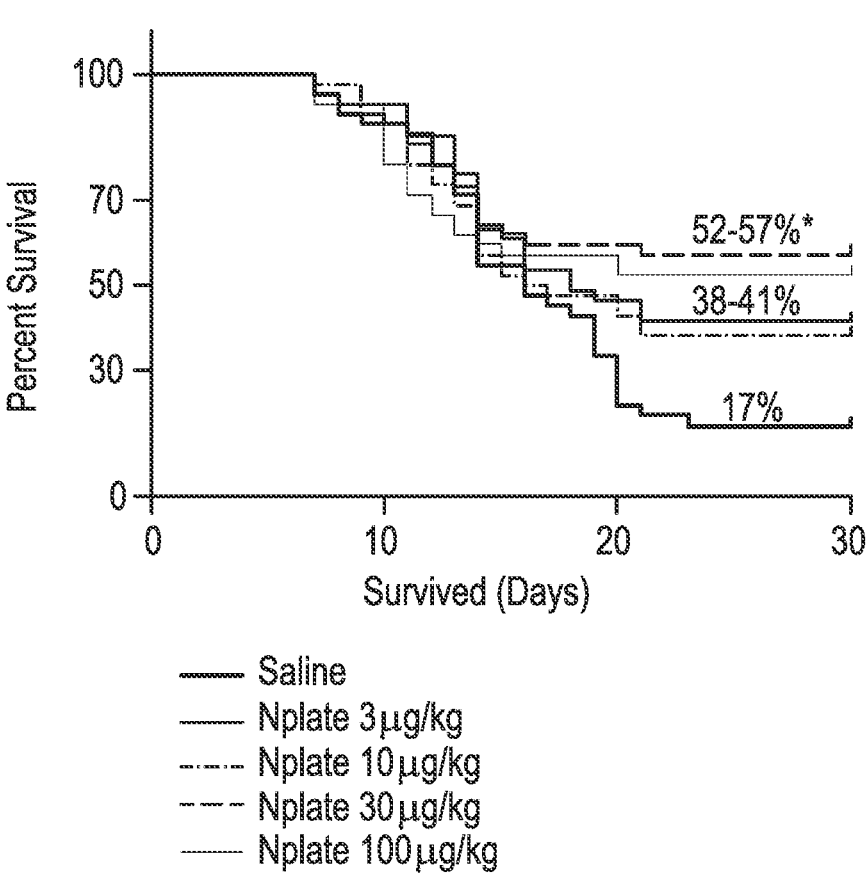
Figure 5B:
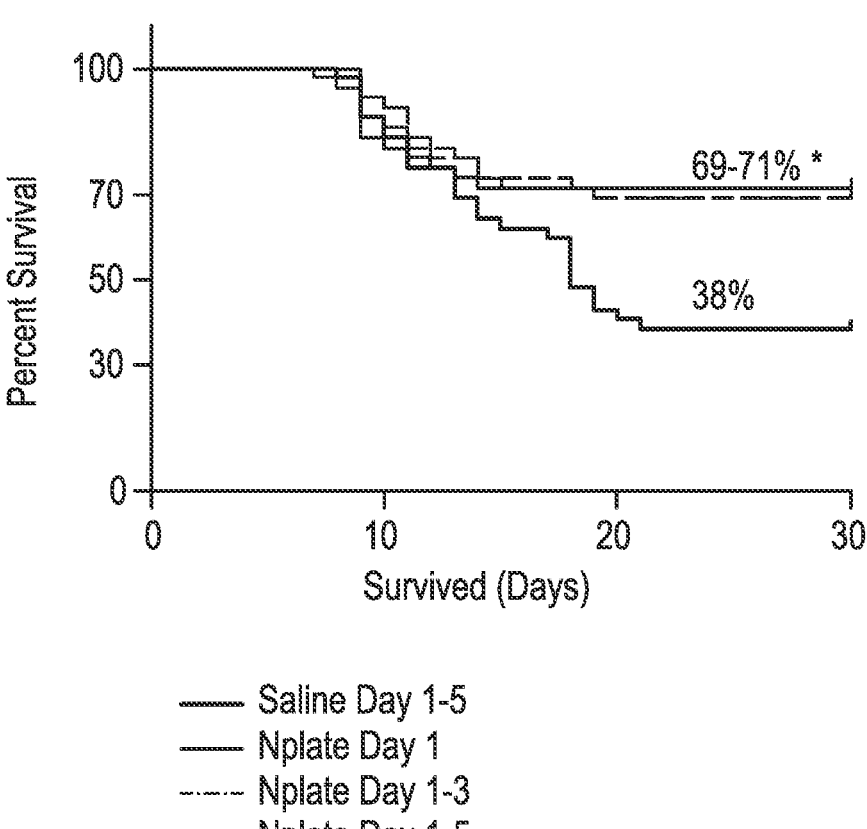
Figure 5C:
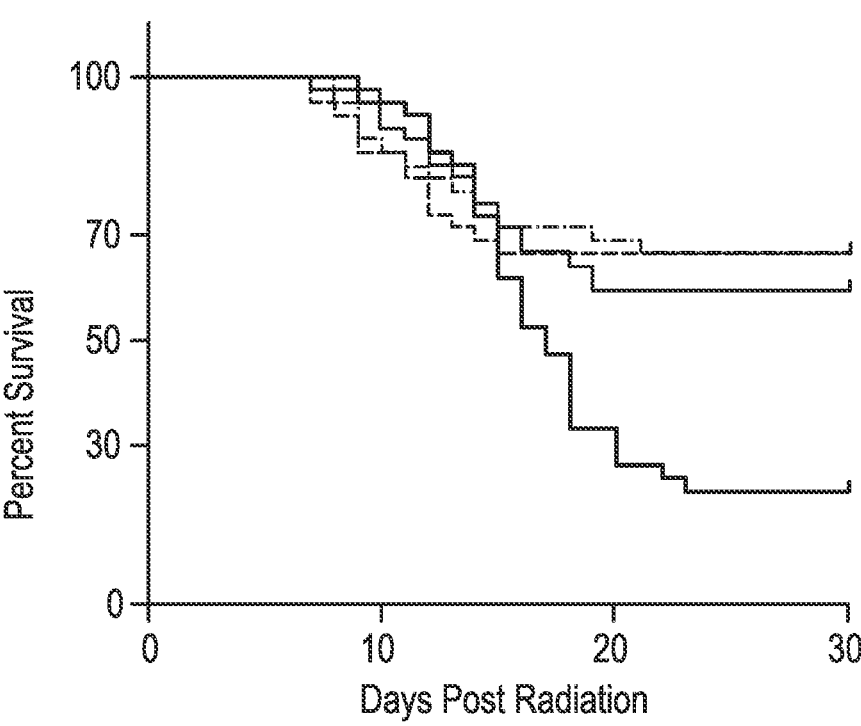

FIGS. 5A-5C. FIGS. 5A and 5B show a romiplostim survival benefit in a mouse HS-ARS efficacy model. FIG. 5A shows a statistically significant 30-day survival benefit of about 40% after a single dose of 30 or 100 μg/kg romiplostim administered 24 h after total body irradiation (TBI). FIG. 5A further shows an about 24% survival benefit observed after 3 or 10 μg/kg (not statistically significant). FIG. 5B shows a statistically significant 30-day survival benefit (about 33%) after 1, 3, or 5 once daily doses of 30 μg/kg romiplostim beginning 24 hours after TBI. Multiple 30 μg/kg doses of romiplostim did not improve survival relative to a single dose of romiplostim. FIG. 5C shows the statistically significant increase in survival with romiplostim (30 μg/kg), pegfilgrastim (300 μg/kg), and their combination. There was no difference in survival benefit when comparing the individual agents to their combination.

Figure 6A:
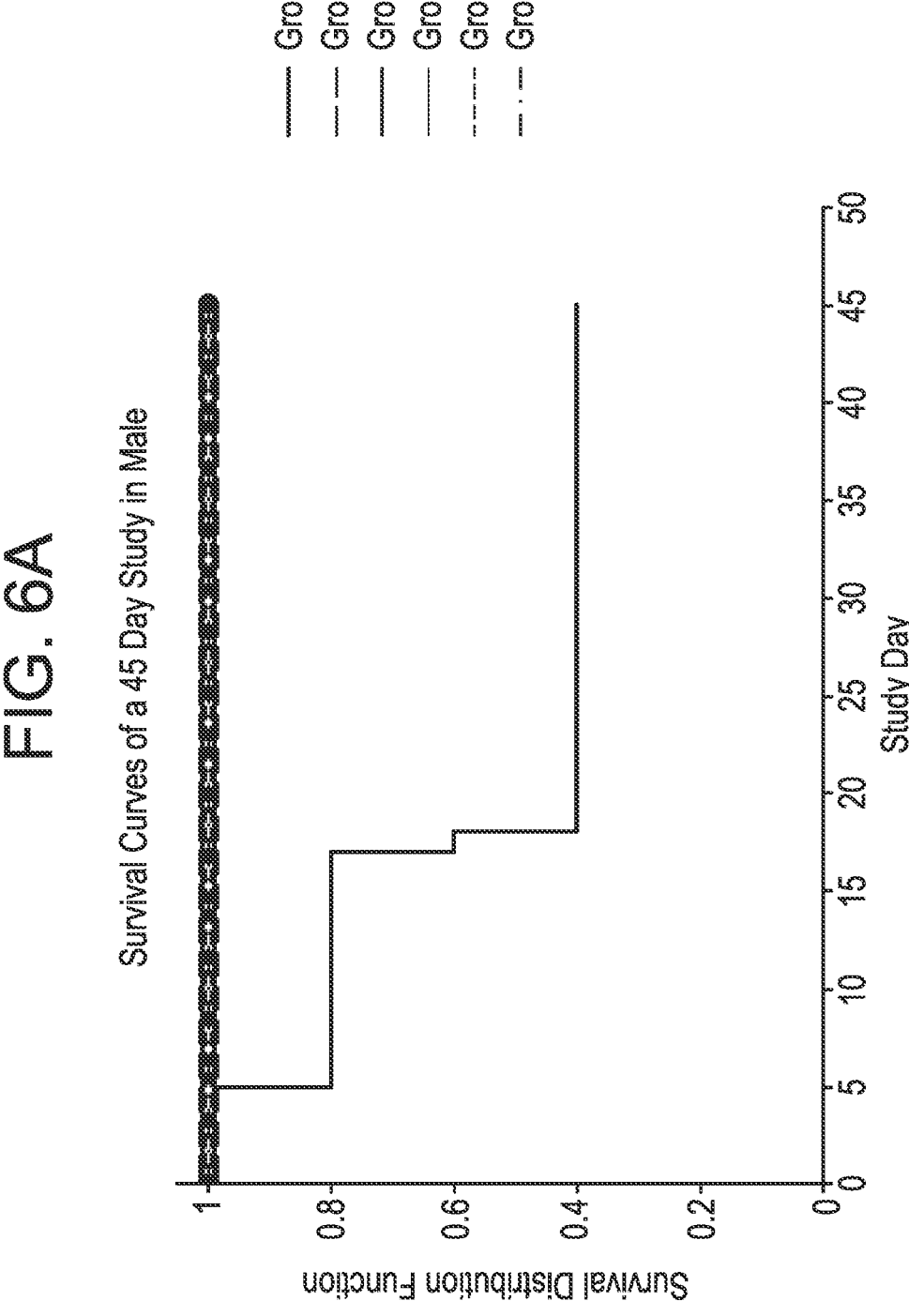
Figure 6B:
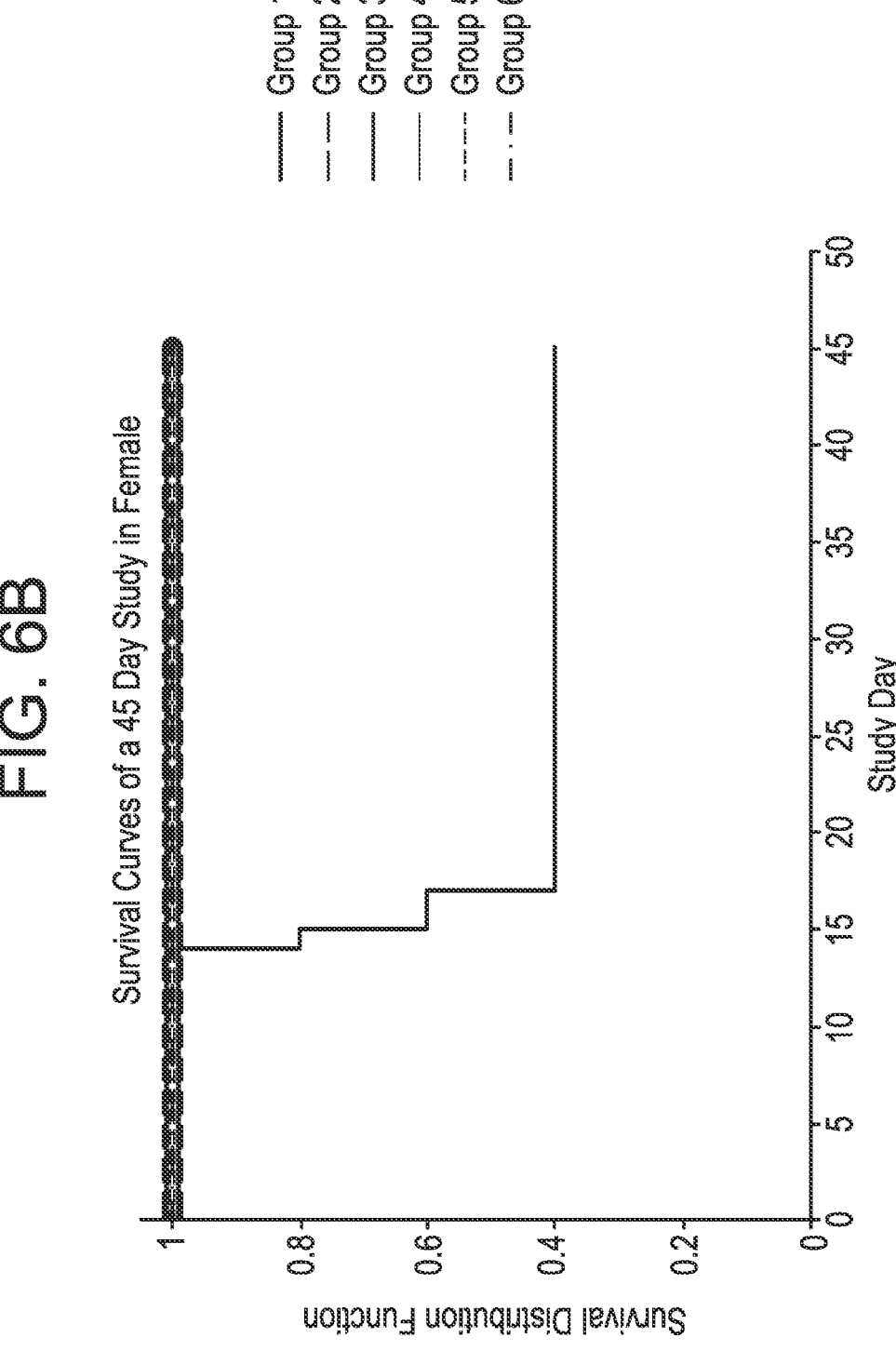
Figure 6C:
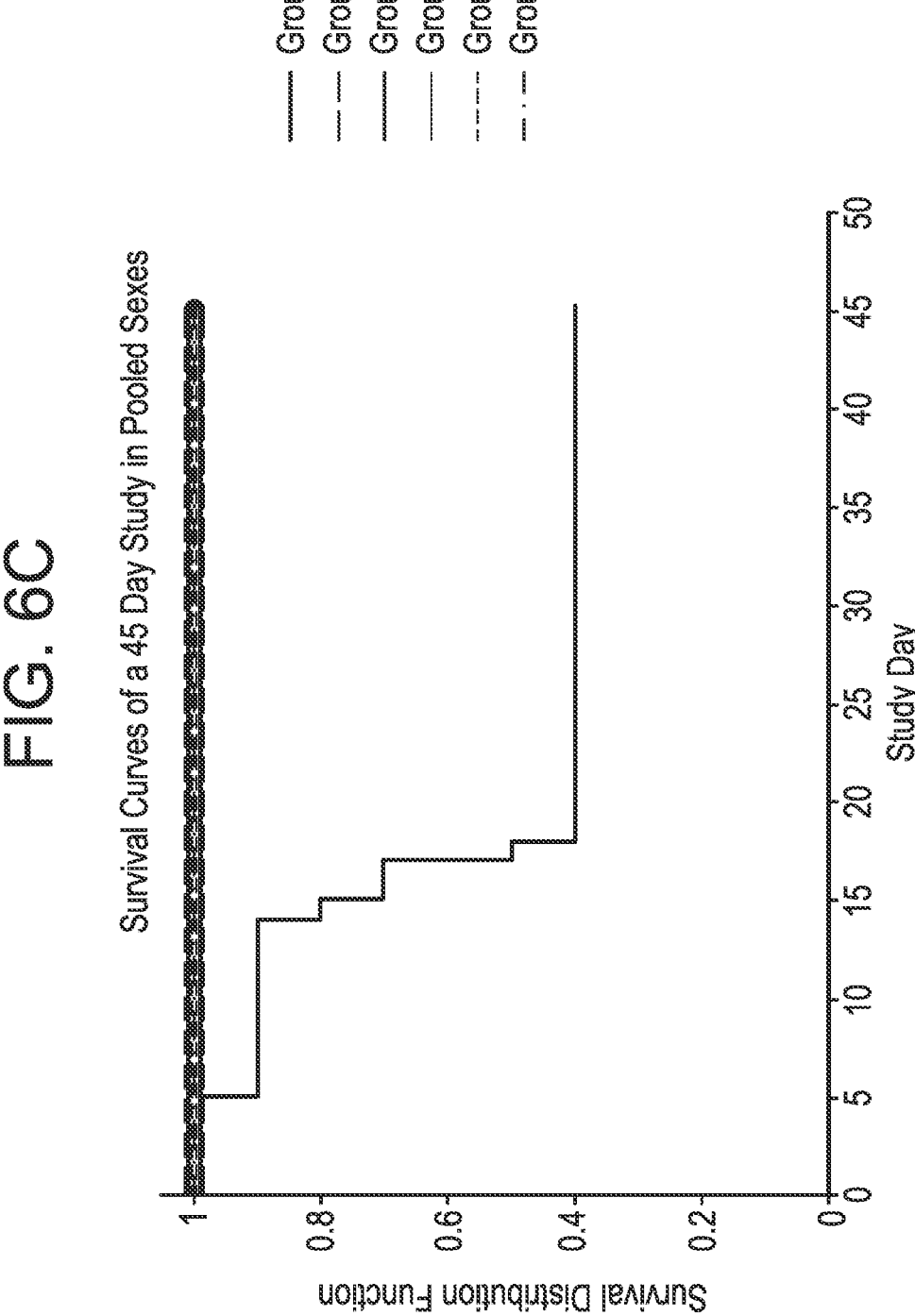

FIGS. 6A-6C present the survival curves (per sex, and sexes combined) in a non-human primate pharmacokinetic/pharmacodynamic study detailed hereinafter. FIG. 6A is the survival curve for males only; 6B, for females only; and 6C, for both sexes combined. There was 40% survival in the irradiated control group and 100% survival in each of the romiplostim or pegfilgrastim treatment groups (sexes combined).

Figure 7:
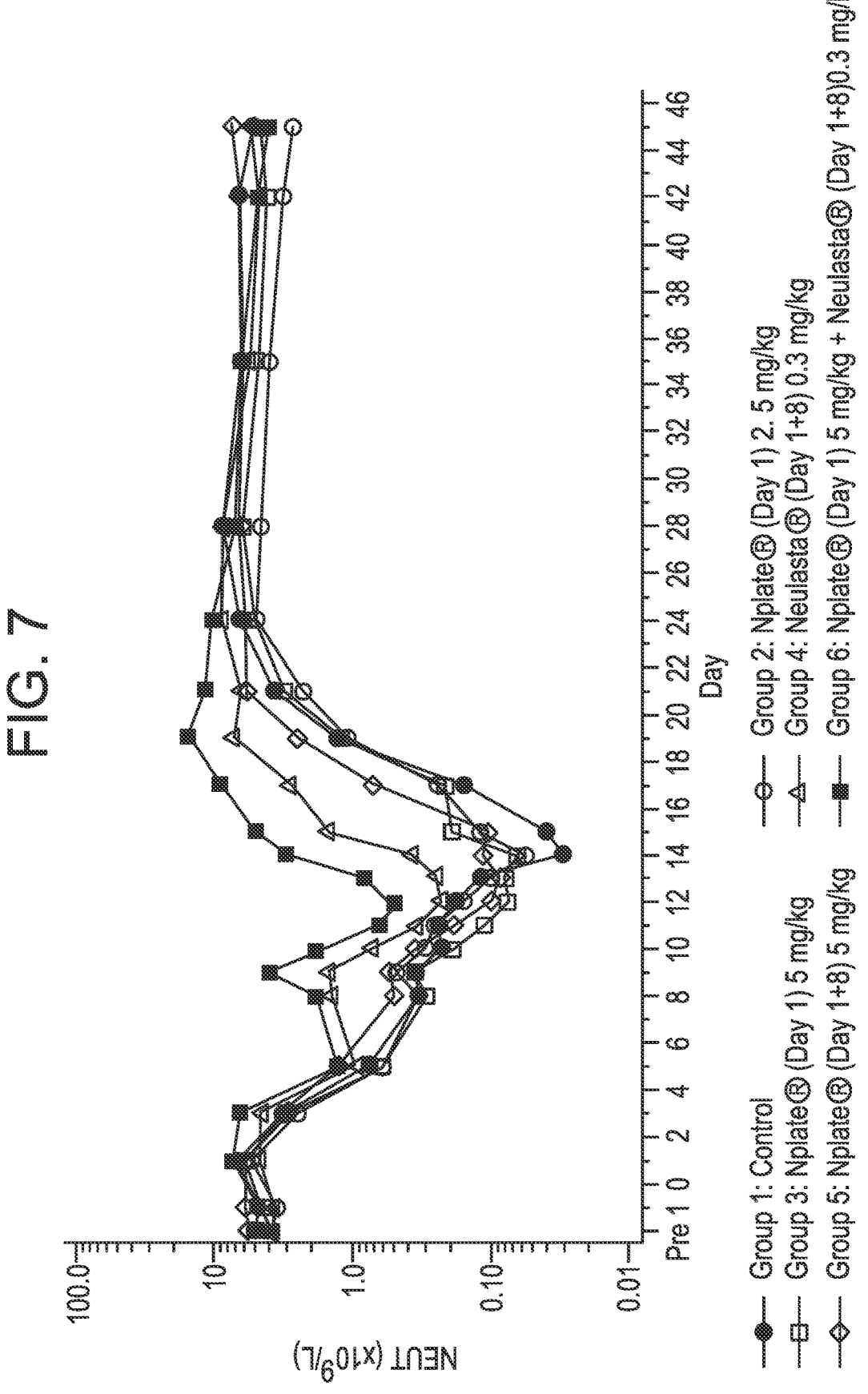

FIG. 7 shows absolute neutrophil counts (sexes combined) in a non-human primate pharmacokinetic/pharmacodynamic study detailed hereinafter.

Figure 8A:
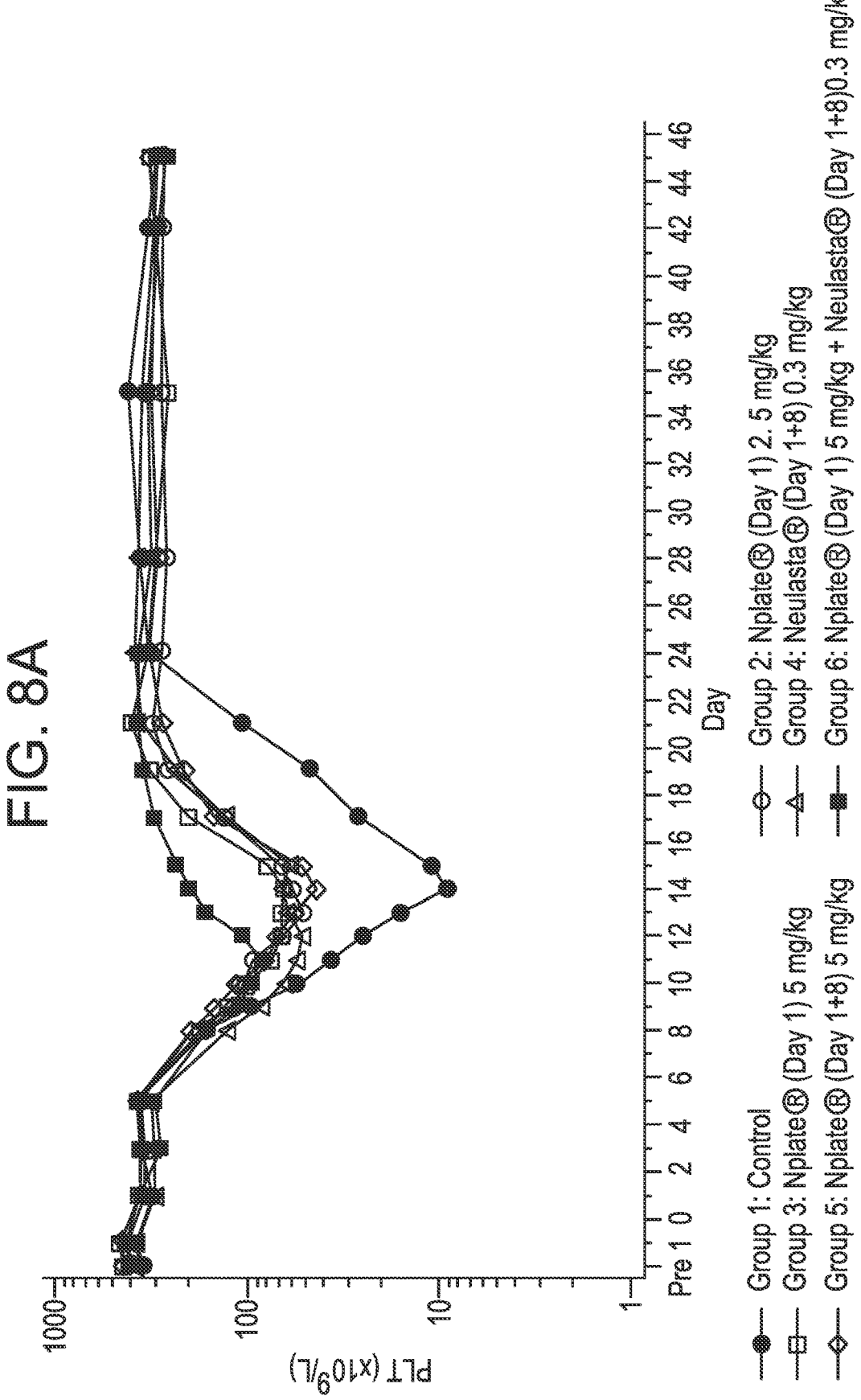
Figure 8B:
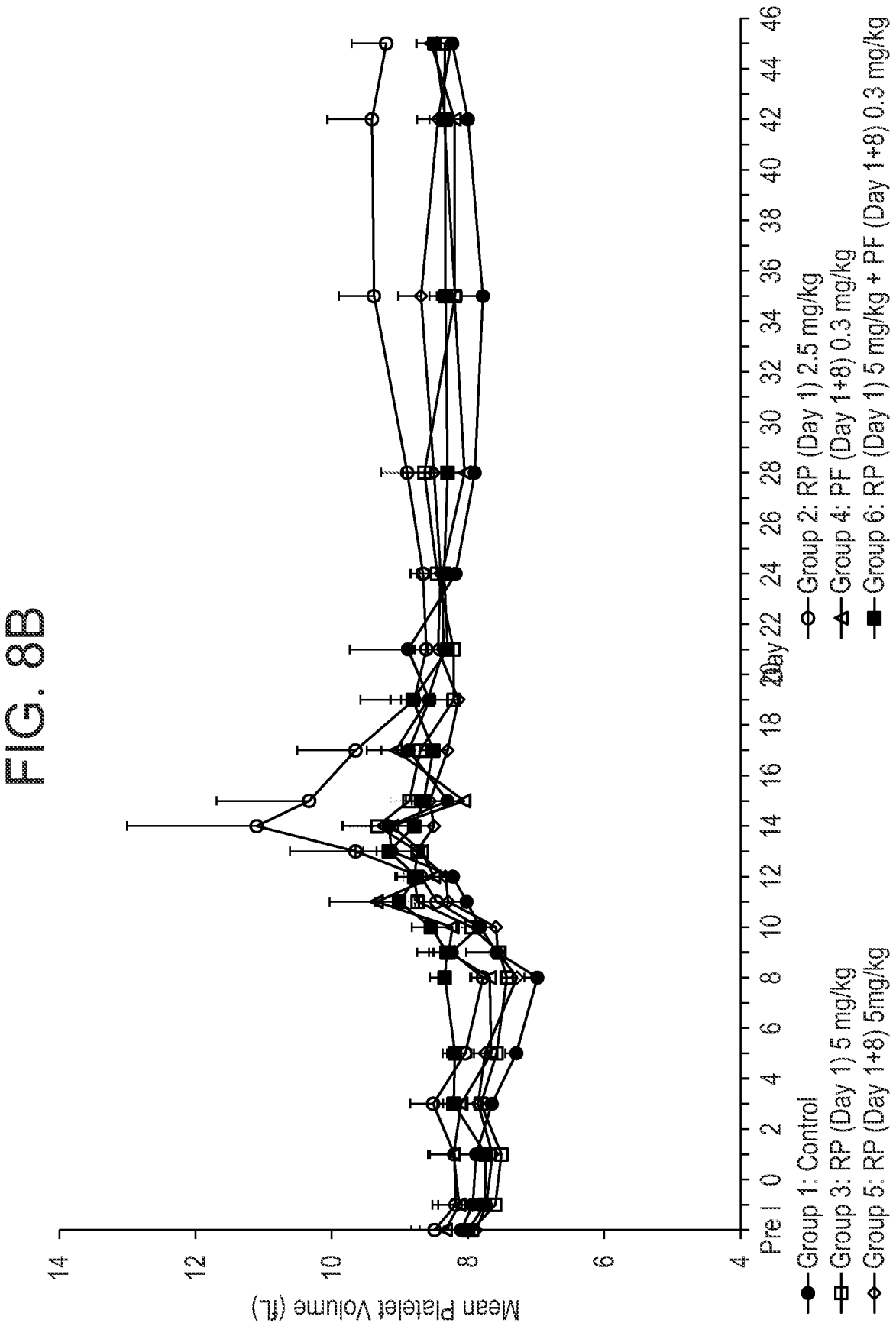

FIGS. 8A-8B. FIG. 8A shows absolute platelet counts (sexes combined) in a non-human primate pharmacokinetic/pharmacodynamic study detailed hereinafter. FIG. 8B shows the mean platelet volume in rhesus macaques over time following irradiation and treatment with either romiplostim (RP), pegfilgrastim (PF) or a combination of both. Error bars+/−standard error. For clarity, the lower error bars were omitted. The legend for FIG. 8A is the same as shown with FIG. 8B (Group 1, n=4-10; Groups 2-6, n=8).

Figure 9:
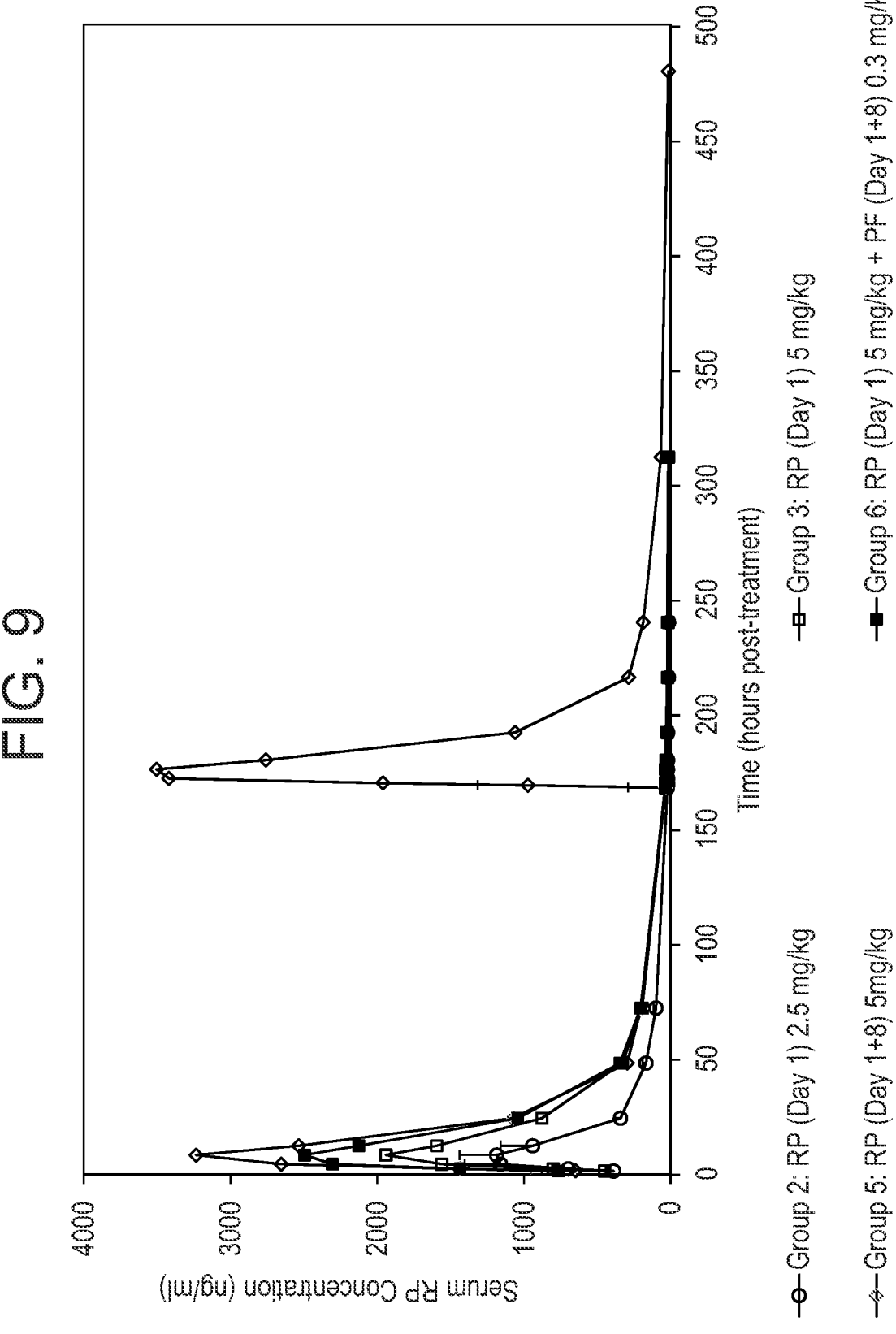

FIG. 9 shows the pharmacokinetics of romiplostim for males and female non-human primates combined. Mean serum concentrations of romiplostim in rhesus macaques over time. RP: romiplostim; PF: pegfilgrastim. (Group 1, n=10; Groups 2-6, n=8).

Figure 10:
Figure 11A:
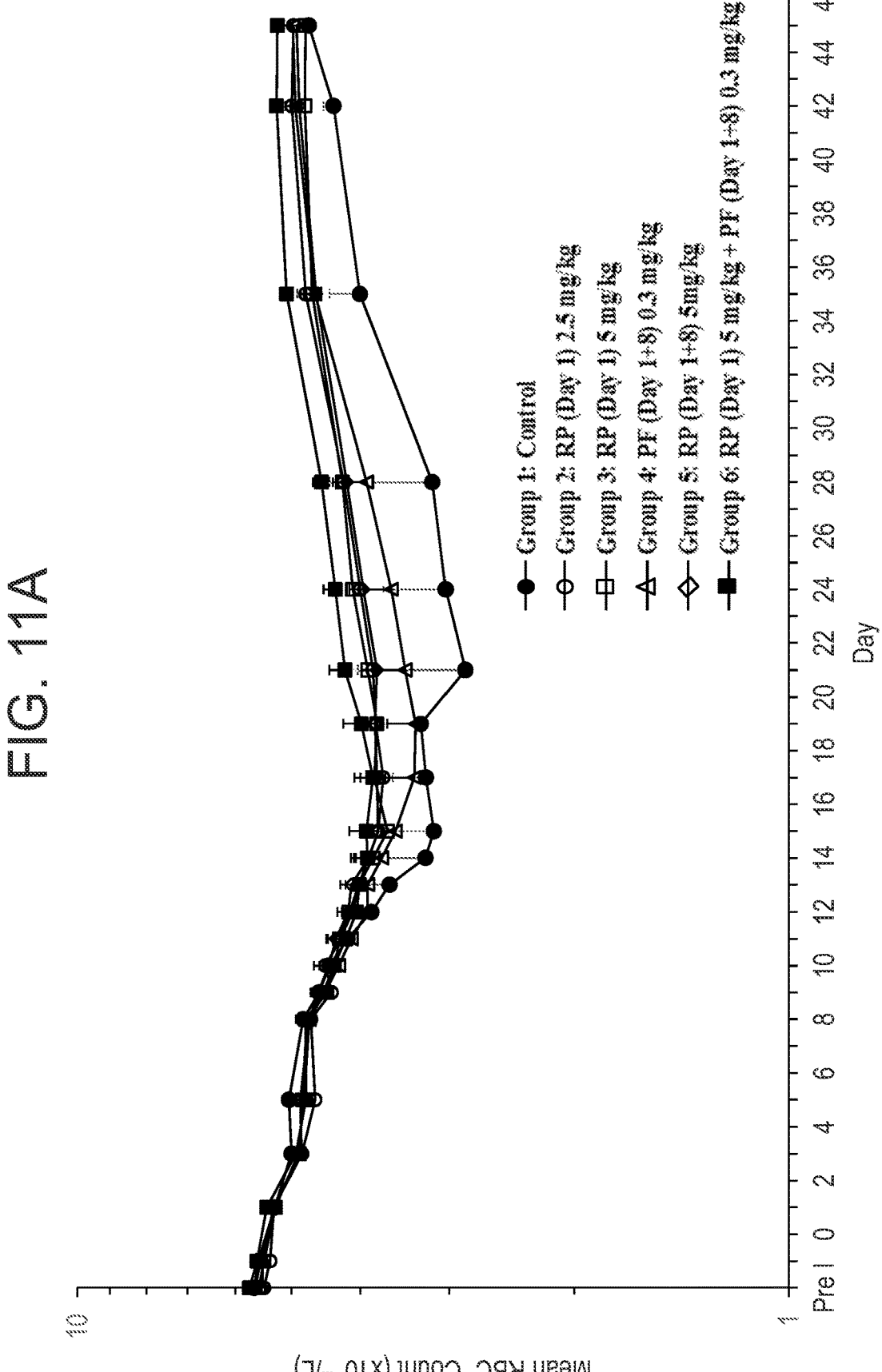
Figure 11B:
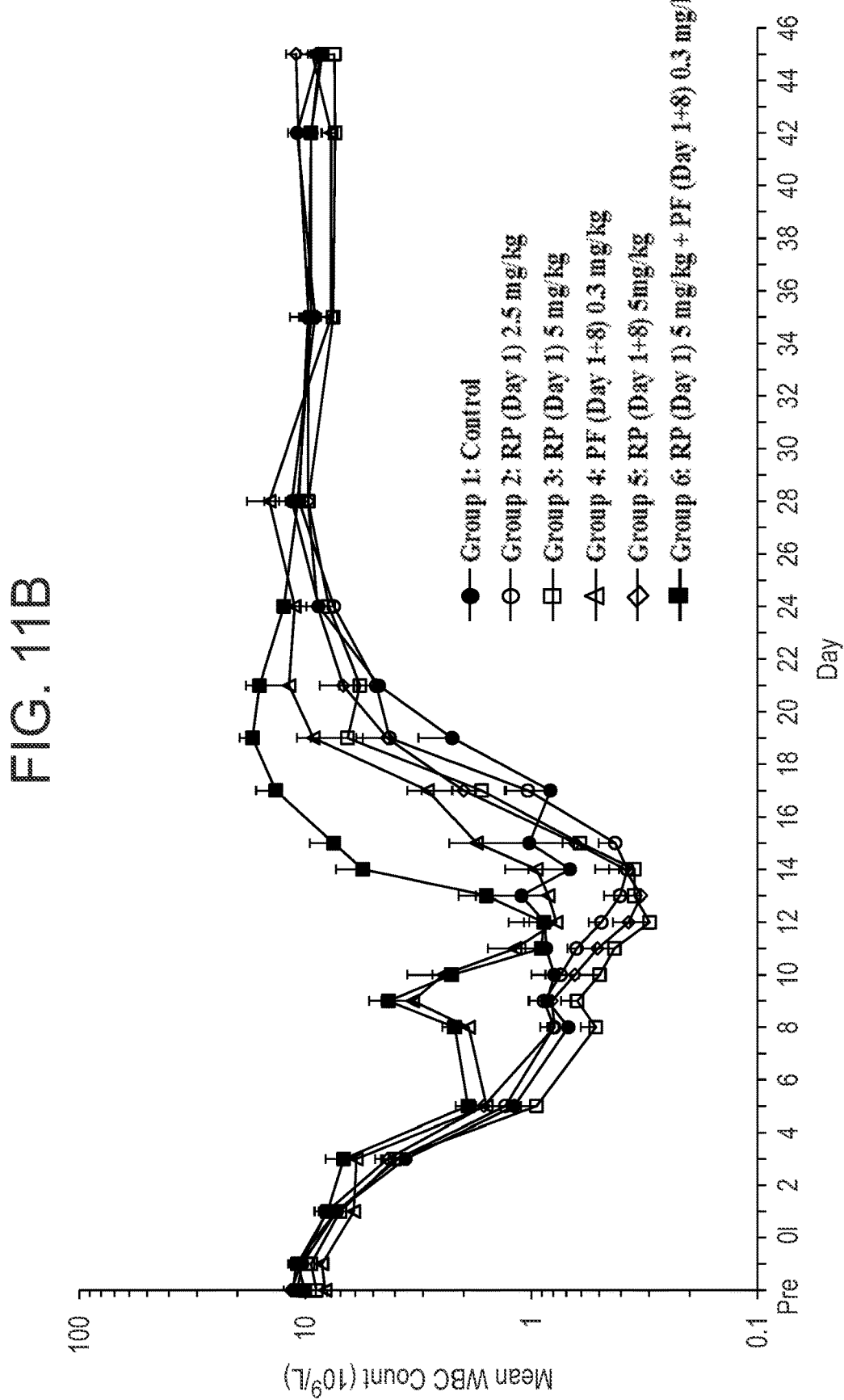
Figure 11C:
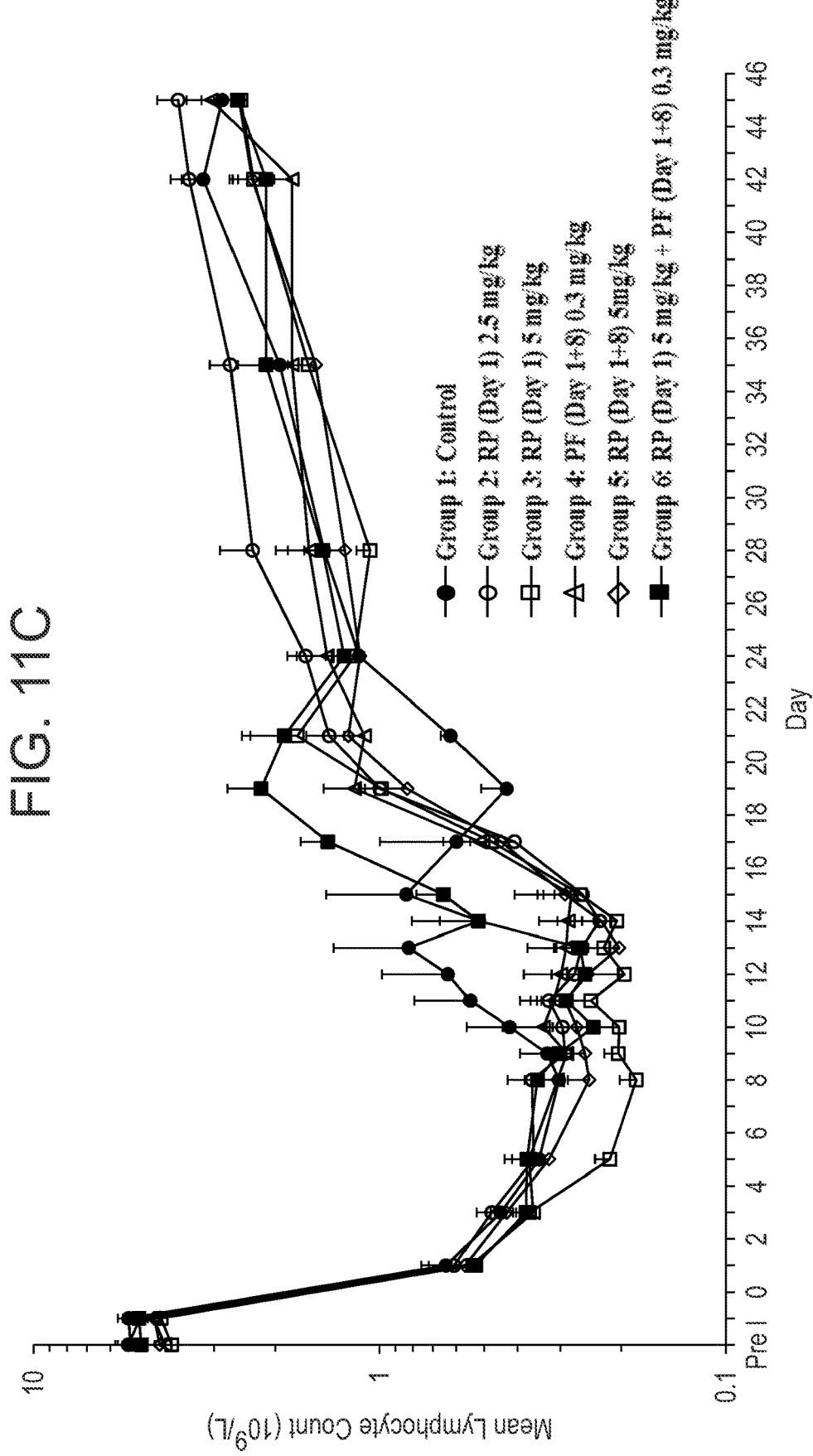
Figure 11D:
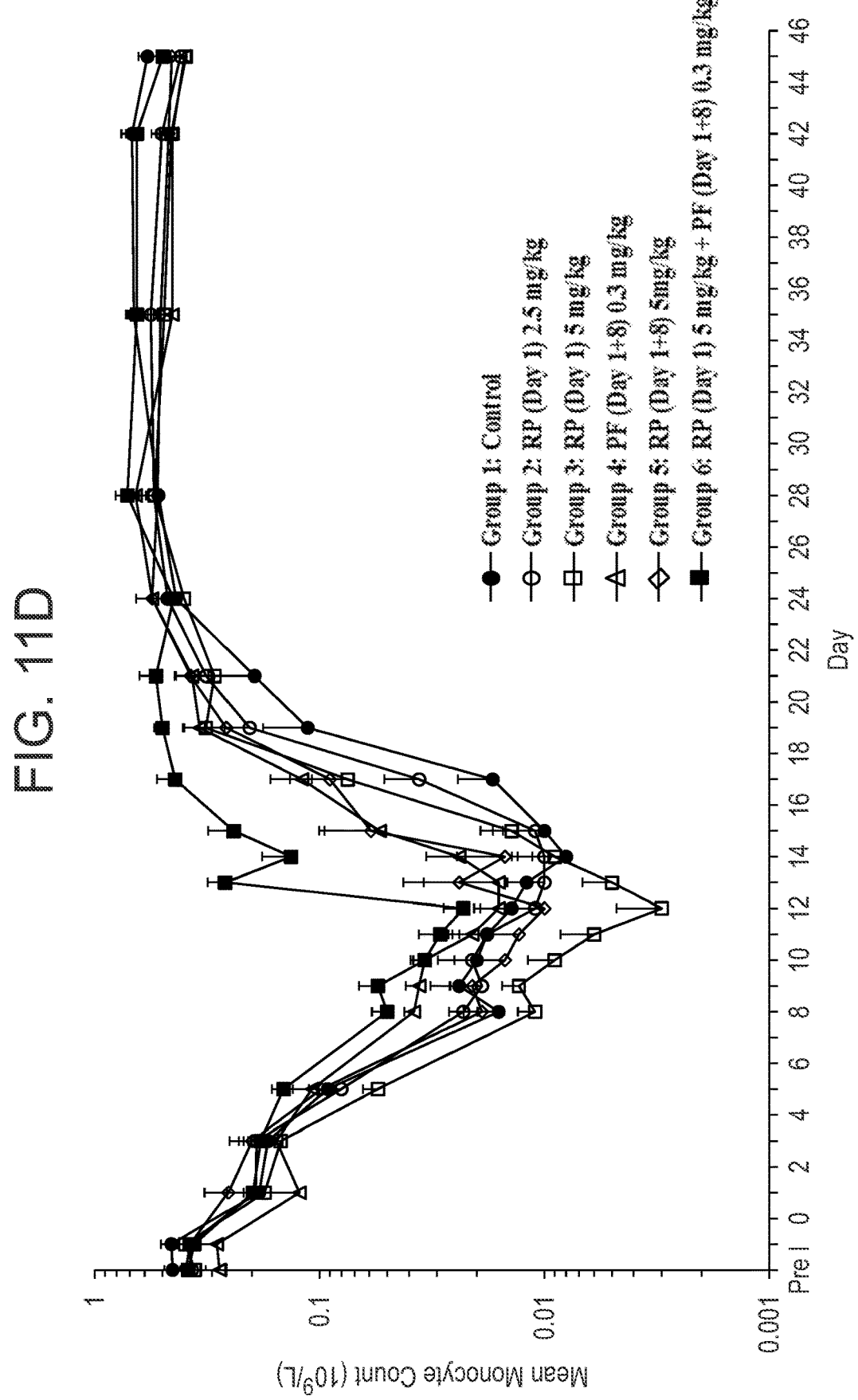
Figure 11E:
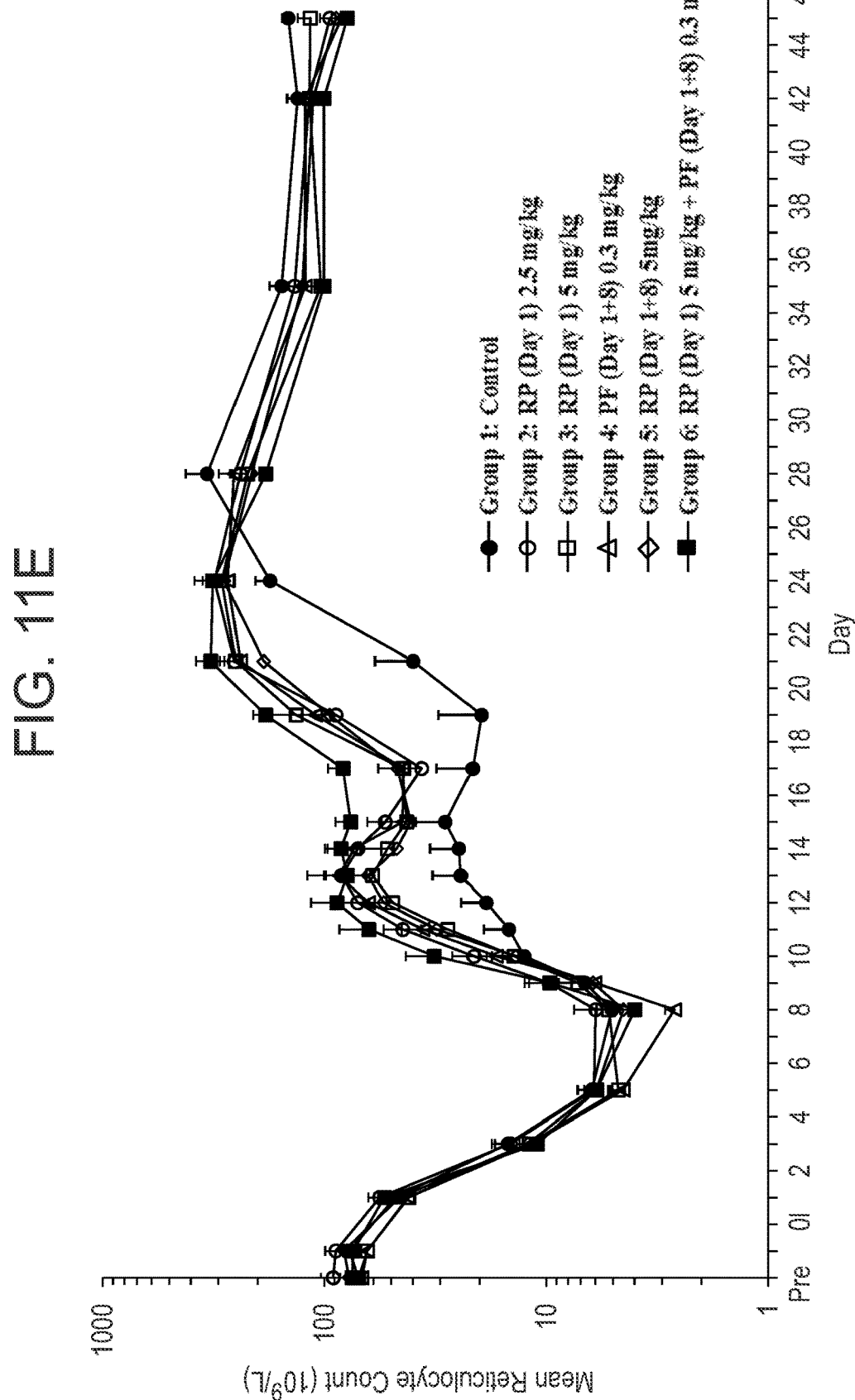

FIG. 10 shows mean absolute body weight of rhesus macaques over time following radiation and treatment with either romiplostim (RP), pegfilgrastrim (PF) or combination of both. Error bars+/−standard error. For clarity, the lower error bars were omitted (Control, n=4-10; Groups 2-6, n=8).

FIGS. 11A-11E show selected hematological parameters in rhesus macaques over time following irradiation and treatment with either romiplostim (RP), pegfilgrastim (PF) or a combination of both. Mean concentrations+/−standard error are shown. For clarity, the lower error bars were omitted. RBC: red blood cell; WBC: white blood cell; (Group 1, n=4-10; Groups 2-6, n=8).

DETAILED DESCRIPTION OF THE INVENTION

This specification reports the results of experiments in a mouse model of ARS and in rhesus macaque monkeys. One of ordinary skill in the art will appreciate that the results demonstrate that romiplostim would be effective in treating radiation exposure from a number of sources. One of ordinary skill in the art will further appreciate that the enhanced benefit observed with pegfilgrastim and romiplostim in HS-ARS studies of non-human primates demonstrate that such enhancement will exist in other conditions characterized by low platelet levels and/or low neutrophil levels.

WORKING EXAMPLES

Example 1

Evaluation of Romiplostim (Nplate®) in Mice as a Potential Countermeasure for Acute Radiation Syndrome
Methods Mice: Male and female C57BL/6J (Jackson Laboratories) 11-12 weeks of age on Day 0. Housed≤3 per cage. Food and water provided ad libitum. Supplemented water-softened chow and hydrogel provided to all mice beginning 4 days after radiation. Study duration≤31 days.

Animals were housed at an American Association for Accreditation of Laboratory Animal Care, international-accredited facility. All research protocols were approved by the Institutional Animal Care and Use Committee.

Radiation: X-ray exposure on Day 0 using Pantak (HF320) unit on conscious mice in individual plastic box-holders. ≤6 mice exposed simultaneously. LD70/30 (dose producing 70 lethality after 30 days) and $LD_{30/30}$ TBI exposures of 680 and 650 cGy, respectively. Dosimetry was performed with PTW-UNIDOS microprocessor controlled universal field class dosimeter. Power levels (230 kVp or 250 kVp, 5 mA, 2 mm aluminum filtration), distance from the exposure beam, and dose rate ~1 Gy/min were held constant. Exposures were performed in the morning with mice on rotating platform (~1 rpm) to ensure uniform dose distribution.

Subcutaneous (sc) injection of saline (vehicle control) or romiplostim at 3, 10, 30, 100 or 300 μg/kg beginning 24 h post-irradiation; 5 ml/kg to a single site. Romiplostim formulation concentration 0, 0.6, 2, 6, 20 or 60 ng/μl. Repeat doses occurred once daily about 24 hours thereafter where applicable.

Blood Collection was from retro-orbital sinus of isoflurane anesthetized mice using $K_3$EDTA anticoagulant for hematology analysis (Siemens Advia 2120). Hematology at scheduled times, male and female data combined, n=1-11/group/time point (n varies because of moribundity).

Serum romiplostim levels were quantified by ELISA with 0.270-0.401 ng/ml LLOQ and 10.9 ng/ml ULOQ (inVentiv Health, Princeton, NJ); n=3 mice/sex/time point/dose group; timepoints=1, 4, 12, 24, 48, 72, and 96 h after romiplostim.

PK analysis: Noncompartmental analysis using Phoenix® WinNonlin® v6.3.

Kaplan-Meier Survival Analysis: GraphPad Prism 6 and StrataSE 14.1; data from both sexes combined (21 mice/sex/group).

Unscheduled Euthanasia: Consistent criteria based on severity scores for adverse clinical signs. Euthanasia was performed upon 30% body weight loss, moribundity, or ≥2 criteria scored as moderate or severe. Adverse signs include:

Abnormal appearance (e.g. ruffled fur, eye or nose discharge, squinting, swelling)

Abnormal postural adjustments or behavior (e.g. hunched posture, ataxia)

Dehydration, hypothermia, hypoactivity

Weight loss relative to pre-study weights (20-29% considered moderate, ≥30% considered severe)

Abnormal physiological functions (urination, defecation, eating, drinking, breathing).

Conclusions

Survival Benefit after Irradiation: A single dose of romiplostim at 30 or 100 µg/kg delivered 24 hours post-irradiation provided approximately a 40% survival benefit. Multiple 30 µg/kg doses of romiplostim did not improve survival relative to a single dose.

Pharmacokinetics (PK): Radiation did not impact romiplostim PK in mice. A 10-fold increase in dose resulted in about a 35-fold increase in $C_{max}$ and $AUC_{last}$. PK increased more than dose proportionally, consistent with nonlinear PK of romiplostim.

Pharmacodynamics (PD): Platelet levels dropped faster, but not as low, in irradiated mice after romiplostim compared with controls (Day 8 vs. Day 10 nadir). Platelet levels recover faster to near baseline after romiplostim administration (Day 22 vs. Day 29). Platelet volume increased after romiplostim administration, suggesting more rapid release of platelets from bone marrow. Other major hematology parameters were affected by radiation but not notably by romiplostim.

Example 2

Evaluation of Romiplostim (Nplate®) and Pegfilgrastim (Neulasta®) in Mice as a Potential Countermeasure for Acute Radiation Syndrome Rapid depletion of white blood cells, platelets (PLT), and reticulocytes are hallmarks of hematopoietic syndrome of acute radiation syndrome (HS-ARS) and, if left untreated, can lead to severe health consequences including death. While pegfilgrastim (Neulasta®) is approved to increase survival in patients exposed to a myelosuppressive dose of radiation, no countermeasure is currently available for the treatment of thrombocytopenia. Romiplostim (Nplate®), a thrombopoietin receptor agonist, is the first FDA-approved thrombopoiesis-stimulating protein for the treatment of low PLT counts in adults with chronic immune thrombocytopenia. The goal of our studies was to evaluate romiplostim as a medical countermeasure to improve survival and PLT recovery following acute radiation in mice.

Single or multiple subcutaneous injection(s) of romiplostim in male and female C57BL/6J mice (n=21M/21F) administered 24 h after total body X-irradiation (TBI) at a LD70/30 dose increased survival and hastened PLT recovery. Full or maximal efficacy with ~40% increase in survival was achieved after a single 30 µg/kg dose of romiplostim. No further survival benefit was seen with higher (30 or 100 µg/kg) or more frequent dosing (3- or 5-daily dosing) of romiplostim, treatment with pegfilgrastim, (300 µg/kg) or combined treatment with pegfilgrastim and romiplostim. In conclusion, a single injection of romiplostim administered at 24 h after TBI is a promising radiation countermeasure that dramatically increased survival, with or without pegfilgrastim, and hastened PLT recovery in mice.

Example 3

Effects of Romiplostim and Pegfilgastim on Acute Radiation-Induced Thrombocytopenia and Neutropenia in the Non-Human Primate Summary:

Neutropenia and thrombocytopenia are recognized as major conditions leading to mortality resulting from acute radiation exposure. In this study, Rhesus macaque monkeys were exposed to total body irradiation from a $Co^{60}$ source and 24 hours later subcutaneously administered control, 2.5 or 5 mg/kg romiplostim (a thrombopoietin receptor agonist), 0.3 mg/kg pegfilgastim (polyethylene glycol-bound to granulocyte-colony stimulating factor; G-CSF, which stimulates neutrophil production) or both romiplostim (5 mg/kg) and pegfilgrastim (0.3 mg/kg).

Results:

Hematology was monitored over a 45-day period post-irradiation. Administration of pegfilgastim or pegfilgastim/romiplostim was associated with a clinically significant improvement in absolute neutrophil count (ANC) nadirs at $0.43 \times 10^9/L$ and $0.57 \times 10^9/L$ for pegfilgastim and pegfilgastim/romiplostim, respectively; compared to ANC nadirs ranging from 0.09 to $0.13 \times 10^9/L$ for the control irradiated animals. Animals administered pegfilgastim/romiplostim also exhibited earlier recovery with higher neutrophil counts compared to pegfilgastim-only group. Severe thrombocytopenia was observed post-irradiation, with a platelet (PLT) nadir of $20.6 \times 10^{12}/L$, 14 days post-irradiation in control animals. All groups administered romiplostim or pegfilgastim had less severe thrombocytopenia, with nadirs on day 11 or 13, ranging from 47.63 to $69.13 \times 10^{12}/L$. Animals administered romiplostim/pegfilgastim presented the least severe nadir in platelet counts (at $92.13 \times 10^{12}/L$) on Day 11, and subsequent earlier recovery with higher PLT counts, compared to other groups. There appeared to be an enhanced benefit from the combination of romiplostim and pegfilgastim, with the combination of both agents associated with the lowest platelet and neutrophil nadirs and also the earliest recovery. Although the study was not designed to show a survival benefit, all treated animals survived to 45 days while 4 of 10 control article-treated animals survived.

The purpose of this study was to provide data of suitable quality and integrity to support applications to the U.S. Food and Drug Administration (FDA) and other regulatory agencies. Therefore, this study complied with the OECD Principles of Good Laboratory Practice (ENV/MC/CHEM(98) 17) as accepted by the U.S. Food and Drug Administration.

The objective of the study was to characterize the pharmacokinetic (PK) and pharmacodynamic (PD) profile of the test item, Nplate® (romiplostim), following one or two subcutaneous administrations to irradiated (target $LD_{30/45}$) Rhesus Macaque non-human primates (NHP), with or without subcutaneous administration of Neulasta® (pegfilgrastim). Animals received supportive care including antibiotics, fluids, anti-ulcer, anti-emetics, analgesics, nutritional support, and wound disinfection according to pre-determined criteria. No blood products were provided.

All animals were exposed to a single uniform total body dose radiation of 550 cGy ($LD_{30/45}$) from a $Co^{60}$ source (Theratron 1000) with a dose rate of approximately 50 cGy/min, for a total exposure time of 10 min 45 sec-11 min 13 sec, in order to achieve a targeted mortality of 30% over 45 days ($LD_{30/45}$). Vehicle, romiplostim, and/or pegfilgrastim were administered by subcutaneous injection to each animal on the dosing days. Administration of romiplostim, pegfilgrastim and/or vehicle began 24 hours±2 hours post irradiation. A table showing the irradiation scheme and number of animals in each dose group is presented in Table 1 and the volumes administered to each group on each dosing day are presented in Table 2.

Blood samples were collected for clinical pathology (hematology and coagulation) from all animals twice during pre-treatment, and on Days 1, 3, 5, pre-dose on 8 (prior to dosing), 9, 10, 11, 12, 13, 14, 15, 17, 19, 21, 24, 28, 35, 42 and 45 for hematology, and on Days 3, 8 (prior to dosing), 10, 14, 17, 21, 24, 28, 35, 42 and 45 for coagulation. Blood samples for pharmacokinetic evaluations were collected pre-irradiation and on Days 1 and 8 at 1, 2, 4, 8, 12, 24, 48 and 72 hours after dosing, as well as on Days 14, 21, 28, 35 and 45. Blood culture was collected non-terminally (when

TABLE 1

Study Design

| Group | Treatment Group | Dose Level | Number of Animals Male | Female |
|---|---|---|---|---|
| 1 | Vehicle Control | 0 | 1001 | 1501 |
| | | | 1002 | 1602 |
| | | | 1003 | 1603 |
| | | | 1004 | 1604 |
| | | | 1005 | 1505 |
| 2 | romiplostim (Day 1) 2.5 mg/kg | 2.5 mg/kg romiplostim | 2101 | 2501 |
| | | | 2002 | 2502 |
| | | | 2003 | 2503 |
| | | | 2004 | 2604 |
| 3 | romiplostim (Day 1) 5 mg/kg | 5 mg/kg romiplostim | 3001 | 3501 |
| | | | 3002 | 3502 |
| | | | 3003 | 3503 |
| | | | 3004 | 3504 |
| 4 | pegfilgrastim (Day 1 + 8) | 0.3 mg/kg pegfilgrastim | 4001 | 4501 |
| | | | 4002 | 4602 |
| | | | 4103 | 4503 |
| | | | 4004 | 4504 |
| 5 | romiplostim 5 mg/kg (Day 1 + 8) | 5 mg/kg romiplostim | 5101 | 5501 |
| | | | 5002 | 5502 |
| | | | 5003 | 5503 |
| | | | 5004 | 5504 |
| 6 | romiplostim 5 mg/kg (Day 1) + pegfilgrastim (Day 1 + 8) | 5 mg/kg romiplostim + 0.3 mg/kg pegfilgrastim | 6001 | 6501 |
| | | | 6102 | 6502 |
| | | | 6003 | 6703 |
| | | | 6004 | 6504 |

TABLE 2

Dose Administration Summary

| Groups | Description | Day 1 romiplostim volume (mL/kg) | Day 1 Vehicle/Ref. Item for romiplostim (mL/kg) | Day 1 pegfilgrastim volume (mL/kg) | Day 8 romiplostim volume (mL/kg) | Day 8 Vehicle/Ref. Item for romiplostim (mL/kg) | Day 8 pegfilgrastim volume (mL/kg) |
|---|---|---|---|---|---|---|---|
| 1 | Vehicle | 0 | 10 | 0 | 0 | 10 | 0 |
| 2 | romiplostim (2.5 mg/kg) | 5 | 5 | 0 | 0 | 10 | 0 |
| 3 | romiplostim (5 mg/kg) | 10 | 0 | 0 | 0 | 10 | 0 |
| 4 | pegfilgrastim | 0 | 10 | 0.03 | 0 | 10 | 0.03 |
| 5 | romiplostim 5 mg/kg (Day 1 + Day 8) | 10 | 0 | 0 | 10 | 0 | 0 |
| 6 | romiplostim 5 mg/kg (Day 1) + pegfilgrastim (Day 1 + 8) | 10 | 0 | 0.03 | 0 | 10 | 0.03 |

Animals were 3 to 6 years old and weighed 3.7 to 6.4 kg at the start of treatment.

During this study, assessments included mortality checks, clinical observations, body weight and body temperature.

febrile neutropenia was identified, or infection was suspected) or at unscheduled termination. Following the last blood collection on Day 45, surviving animals were released from the study.

There were 6 mortalities during the conduct of the study, 3 males and 3 females, all from Group 1 (vehicle). The clinical signs leading up to termination or death included severe hemorrhaging, severely decreased activity and hypothermia. Three animals (two males and one female) were found dead on Days 5, 14 and 18. The male found dead on Day 5 was noted to present moderately decreased appetence, slight tremors and hematochezia, the day prior to death. The remaining 3 animals were euthanized prior to scheduled termination on Days 15 and 17.

Subcutaneous administration of vehicle following total-body irradiation at 550 cGy, resulted in a 60% mortality $LD_{60/45}$ in control animals with no mortalities seen in any of the romiplostim or pegfilgrastim groups. This mortality was higher than the targeted $LD_{30/45}$.

Clinical signs, body weight changes, and body temperature changes expected in the radiation model were observed to be of lesser severity and/or incidence in the treated groups relative to the vehicle control group, with Group 6 showing earlier recovery and improved body weight recovery compared to the other treated groups. As expected, there were no significant changes in coagulation parameters in the control and treated groups post-irradiation.

Hematology parameters (RBC, HCT, WBC, LYMPH, MONO) showed the expected decreases post-irradiation, with all treated groups presenting earlier and improved recovery, compared to the control group. Generally, Group 6 (dosed with both romiplostim and pegfilgrastim) was noted to have earlier recovery with milder radiation induced effects compared to the other treated groups. NEUT (neutrophil) and PLT (platelet) levels decreased as expected post-irradiation. Group 4 and 6 (both dosed with pegfilgrastim), showed earlier recovery of NEUT compared to the rest of the treated groups (as expected, as pegfilgrastim stimulates neutrophil production), however Group 6 (dosed with both romiplostim and pegfilgrastim) was noted to have earlier recovery on Day 13 with higher counts ($1.25 \times 10^9$/L) compared to Group 4 (pegfilgrastim alone, $0.51 \times 10^9$/L, Day 13). PLT nadirs were less severe in the treated groups; however, Group 6 had the least severe PLT nadirs with cell count at $92.1 \times 10^9$/L (nadir on Day 11) and the earliest recovery ($105.5 \times 10^9$/L, Day 12). These results were significantly different ($p \leq 0.01$) from Groups 1 and 4. Although the animals in Group 5 were dosed twice with romiplostim, when compared to Group 3 (romiplostim administered once), no significant difference was observed for NEUT or PLT counts at nadir or start of recovery. Based on these results, there appears to be a synergistic effect on the NEUT and PLT when romiplostim and pegfilgrastim were co-administered.

Considerable variability was observed in serum romiplostim concentrations between animals in several dose groups that resulted in substantial variability in PK parameters. The serum exposure of romiplostim, based on mean $C_{max}$ and $AUC_{last}$ values, increased by over 80% in females and decreased by ~15% in males in Group 6 when compared to values from Group 3. A dose increment from 2.5 to 5 mg/kg of romiplostim resulted in a disproportionate increase in serum exposure of romiplostim. There was a trend toward accumulation of romiplostim with repeat administration, which was also more evident in females, as ~43% greater mean $C_{max}$ and ~36% greater $AUC_{(0-72\ hr)}$ were observed in females after administration of Dose 2 when compared with Dose 1. When compared to Group 3, a significant increase ($p \leq 0.01$) in PLT was only observed on Days 14 and 15. Justification for Dose Level for Romiplostim and Pegfilgrastim

The dose levels chosen for romiplostim were based on the previously conducted single and repeated dose toxicology studies in normal, healthy NHPs. The range of doses selected was anticipated to achieve clinically-relevant increases in platelets. The highest dose selected was the maximum administrable dose based on limitations on dosing volume and dosing formulation. The dose level chosen for pegfilgrastim was based on previous NHP studies showing clinically-relevant increases in neutrophils to support licensure of the product for acute radiation syndrome (ARS).

Justification for Irradiation Level

An irradiation dose level of 550 cGy was selected based upon available data and historical data from studies conducted at Citoxlab North America to result in ~$LD_{30/45}$. This dose was intended to provide an assessment of PK/PD in the presence of irradiation yet still provide an adequate level of survival to provide a meaningful dataset.

Reason for Choice of Route of Administration

The subcutaneous route is the intended route of administration of the test items in humans.

Reason for Choice of Test System

The Rhesus macaque (*Macaca mulatta*) was selected as it is an accepted species for PD and PK profiling. Abundant historical data is also available after irradiation in rhesus monkeys and supports the use of this species for the study.

Justification for Numbers of Animals Selected

The number of animals used on the study was considered the minimum required to achieve the study objectives, based on regulatory requirements, statistical power and/or availability of historical data and were within IACUC approved guidelines.

Characterization of Test Item, Diluent, and Vehicle/Reference Item

Test Item 1

Identity: romiplostim (lyophilized powder in vial, 600 µg/vial; 0.5 mg/mL once reconstituted with 1.2 mL sterile water for injection; also known as romiplostim and AMG 531)

Batch No.: 0010294965

Retest date: Oct. 31, 2018

Storage conditions: Refrigerated, 2 to 8° C. and protected from light

Test Item 2

Identity: pegfilgrastim (also known as pegfilgrastim)

Lot No.: 0010236097

Expiry date/Retest date: March 2018

Storage conditions: Refrigerated, 2 to 8° C. and protected from light

Diluent for Romiplostim

Identity: Sterile Water for Injection, USP

Lot: W7J18A0

Expiry date: October 2018

Vehicle/Reference Item for Romiplostim

Identity: 0.9% Sodium Chloride for Injection USP

Lot: W7B10C1

Expiry date: May 2018

Preparation of Dosing Formulations

Romiplostim test item formulations were prepared using sterile reagents and clean technique in a laminar flow hood. The dosing solutions were protected from light, maintained on wet ice or refrigerated until administration, and administered within 20 hours of preparation. On the day of use, romiplostim was reconstituted at a concentration of 500 µg/mL (0.5 mg/mL) by adding 1.2 mL sterile water for injection to each vial via syringe. The vials were gently swirled and inverted to reconstitute, then inspected to confirm that the solution was clear and colorless, prior to pooling the volume of all the reconstituted vials into a sterile container. The sterile container was then capped with a rubber septum after removal of the analytical chemistry samples.

The pegfilgrastim test item formulations were allowed to come to room temperature (protected from light) for at least 30 minutes prior to administration, pooled into a sterile container with a rubber septum and used as is.

Dose Analysis of Formulated Romiplostim

Concentration analyses of the reconstituted test item romiplostim was performed for this study. Samples from the formulated romiplostim dosing solution (1 mL in duplicate) were taken on the days of dosing for concentration analysis. The samples were stored refrigerated (targeted 4° C.) prior to analysis. Homogeneity analysis was not conducted as the formulated product is an aqueous solution. Equivalent samples were collected from the vehicle formulation. Concentration of the dose formulations were confirmed to be within a ±10% acceptance criteria using a validated method. No dose formulation analysis was conducted on pegfilgrastim because it was used as supplied.

Administration of Dosing Formulations

Romiplostim and vehicle/reference items were administered by subcutaneous injection in the upper back and/or lumbar area using a 25-gauge needle attached to a syringe as detailed in study design tables above (Tables 1 and 2). The actual volume administered to each animal was calculated and adjusted based on the most recent practical body weight of each animal.

Injections were given in multiple sites on the upper back and/or lumbar area. romiplostim and/or vehicle/reference item were divided and administered by subcutaneous injection on Days 1 and 8 over 6 sites. Pegfilgrastim was administered at a separate 7th site on the upper back (above the level of the $1^{st}$ and $2^{nd}$ sites) on both Day 1 and Day 8.

The injection sites were shaved and tattooed prior to dosing (approximately 1.5×1.5 cm square per site). Only animals to be dosed with pegfilgrastim were tattooed for a 7th dose site. Dosing syringes were filled from the sterile container and warmed just prior to injection for each animal.

On occasions during the dosing period, individual animals had small amounts of dose formulation leakage from the dosing site or were dosed intra-dermally as presented in Table 3.

TABLE 3

Summary of Dosing Site Observations

| Group | Animal Number | Day 1 | Day 8 | Formulation Type |
|---|---|---|---|---|
| 1 | 1001 | | ✓ | Vehicle |
| | 1002 | ✓ | | Vehicle |
| | 1501 | ✓ | ✓ | Day 1 and Day 8: Vehicle |
| | 1602 | ✓ | | Vehicle |
| | 1505 | | ✓ | Vehicle |
| 2 | 2101 | ✓ | | romiplostim |
| | 2002 | ✓ | | Vehicle |
| | 2501 | | ✓ | Vehicle |
| | 2502 | ✓ | | Vehicle |
| | 2604 | | ✓ | Vehicle |
| 3 | 3001 | * | | romiplostim |
| | 3003 | | ✓ | Vehicle |
| | 3004 | ✓ | | romiplostim |
| 4 | 4002 | | ✓ | Vehicle |
| | 4103 | ✓ | | pegfilgrastim |
| | 4503 | | ✓ | Vehicle |
| 5 | 5002 | ✓ | | romiplostim |
| | 5501 | ✓ | | romiplostim |
| | 5503 | ✓ | | romiplostim |

TABLE 3-continued

Summary of Dosing Site Observations

| Group | Animal Number | Day 1 | Day 8 | Formulation Type |
|---|---|---|---|---|
| 6 | 6001 | ✓ | | romiplostim |
| | 6003 | | ✓ | Vehicle |
| | 6501 | ✓ | | romiplostim |
| | 6504 | | ✓ | Vehicle |
| | 6703 | ✓ | ✓ | Day 1: romiplostim; Day 8: vehicle |

✓: small amount of formulation observed outside the injection site
* small amount of romiplostim injected intra-dermally On Day 1, Animal 4602 (Group 4, pegfilgrastim) was dosed with higher volumes of vehicle and pegfilgrastim, than what was calculated based on the body weight of the animal (51 mL instead of 37 mL vehicle, and 0.15 mL instead of 0.11 mL of pegfilgrastim, representing +36% of the nominal dose). Subsequent evaluation of the clinical condition and the hematology analysis of the animal over the course of the post dose did not reveal any adverse effects on the increased fluid volume administered subcutaneously and the animal's neutrophil counts were comparable to the other animals in the same group. Due to the animal's condition and hematology results being comparable to others in the same group, and that the Group 4 animals had serum analyzed as reference control samples, the increased dose volume had minimal to no impact on animal welfare or the study objectives. These dosing deviations were not considered to have an impact on the results and study integrity, since the volume was considered minimal compared to the amount administered.

Test System

Fifty (50) Rhesus monkeys (25 males, 25 females), including 2 spare animals/sex, were received from Kunming Biomed International Ltd (China) and transferred onto study on Jan. 15, 2018. At the onset of dosing, the age of the animals ranged from 3 to 6 years. The body weights ranged from 3.8 to 6.4 kg and from 3.7 to 5.5 kg for males and females, respectively Total Body Irradiation Animals from Groups 1 to 6 were exposed to a single uniform total body dose radiation from a $Co^{60}$ source (Theratron 1000) with a dose rate of approximately 50 cGy/min. The nominal irradiation dose of 550 cGy was provided to the radiophysicist for calculation of the exposure times. Exposure times and assigned radiation doses were verified by two different reviewers prior to animal irradiation to ensure accuracy of the radiation treatment plan. Dosimetry analysis showed that the mean dosimetry measurements were consistent throughout the groups ranging from 514 to 562 cGy with Nanodots and from 541 to 546 cGy with the Farmer Ionization Chamber.

Prior to the day of irradiation, the radiation dose was calibrated using an acrylic phantom placed in the same experimental set up used for animal irradiation. Animals in each replicate were irradiated in a random order. Exposure time for each animal was calculated individually based on body dimension.

Two dosimeters (Landauer, Inc. Model Nanodot) were placed on each animal prior to the whole-body irradiation to quantify the dose. On the day of irradiation, one dosimeter was placed on the midplane approximately at the level of the xiphoid process and a second dosimeter was placed at the corresponding level in the dorsal area, below the interscapular area. Dosimeters were placed under a gel bolus build-up of approximately 5 mm (superflab) and secured with bandaging. The dosimeters were returned to Landauer for estimation of exposure. Dosimetry measurements using phantoms, the dose rate, duration of irradiation and the actual time of irradiation for each individual animal were documented.

A Farmer ionization chamber was connected to an electrometer and included in each radiation treatment field to provide a quantification of the radiation dose. The energy recorded by the electrometer was converted to a radiation dose and included in the study report. The ambient temperature and atmospheric pressure were recorded after each irradiation for calculation of real-time dosimetry.

Animals were fasted overnight prior to total-body irradiation and fed after irradiation at the irradiation facility (i.e., a banana was given after irradiation to each animal) and upon return to the facility.

Prior to irradiation, each animal was anesthetized with ketamine (10 mg/kg, IM) and transferred to the irradiation treatment room. An additional dose of anesthetic was given when needed. Soft music was provided inside the treatment room to reduce stress to the animals. Animals were placed in a horizontal position for total body irradiation. Animal positioning was confirmed with linear markers installed in the treatment room.

In order to produce homogenous dose distribution, treatment was divided in two parts. First, the animals received half of the dose by antero-posterior (AP) irradiation. The second half of the dose was delivered by postero-anterior (PA) irradiation. Fluid therapy (10 mL/kg Lactated Ringer's; IV) was provided post-irradiation to each irradiated animal to help manage hypotension.

In-Life Observations

Mortality

Mortality checks were recorded concomitantly with the cage-side clinical signs observations during all phases of the study. Some animals in unrelievable pain or distress were euthanized when possible. Clinical pathology blood samples, hemoculture and PK samples were taken from animals euthanized prematurely, when possible. Any data collected at unscheduled euthanasia was excluded from any group mean summary.

Hematology/Pharmacodynamics (PD) and Coagulation

Clinical pathology evaluations (hematology and coagulation) were performed on all animals as indicated below. Blood samples were collected from a femoral vein (cephalic or saphenous vein were also used when necessary) from animals that were not fasted. The femoral vein was not used between Days 6 and 24, except when an individual's platelet count was >$80 \times 10^9$/L. Prior to any blood collection (starting post-irradiation), a wipe of isopropyl alcohol 70% followed by a wipe of chlorhexidine gluconate 4% was done at the blood collection site. Gauze with a small quantity of isopropyl alcohol 70% was kept in place after each blood collection and pressure to the collection site was applied manually. When complete hemostasis was achieved, the area around the bleeding site was wiped again with isopropyl alcohol 70%.

In addition to the scheduled collections, on Days 10 and 14, Group 6 Animals 6102 and 6501, respectively, were bled (5 mL each) due to technicians being injured by these animals, as part of the test facility Health and Safety standard operating procedures.

a) Hematology/PD

Hematology evaluations were performed on all surviving animals twice during the pre-treatment period (between Days −12 to −5), and post-radiation exposure on Days 1, 3, 5, pre-dose on 8, 9, 10, 11, 12, 13, 14, 15, 17, 19, 21, 24, 28, 35, 42 and 45.

Except for pre-treatment sample collections, no repeat hematology or coagulation collections were performed to avoid any potential impact on outcome. Any animal that was authorized for unscheduled euthanasia had blood collection attempted for hematology and coagulation, only when sampling had not already been collected for that day.

The following parameters were measured on blood samples collected into tubes containing $K_3$EDTA as anticoagulant. The target volume of blood collected for each sample was 0.5 mL.

| | |
|---|---|
| Hematocrit | Platelet Distribution Width |
| Hemoglobin | Platelet count |
| Hemoglobin distribution width | Plateletcrit/thrombocrit |
| Mean corpuscular hemoglobin | Red blood cell count |
| Mean corpuscular hemoglobin concentration | Red cell distribution width |
| | Reticulocyte counts (absolute and relative) |
| Mean corpuscular volume | White blood cell count (WBC) |
| Mean Platelet Volume | WBC differential (absolute + relative) | b) Coagulation

Samples (1.0 mL in citrate tubes) were taken once during the pre-treatment period, and on Days 3, pre-dose on 8, 10, 14, 17, 21, 24, 28, 35, 42 and 45. The following parameters were noted:

Activated partial thromboplastin time

Prothrombin time

Fibrinogen

Sample Appearance (when abnormal)

Any remaining blood or plasma, following the hematology or coagulation analysis or any unanalyzed samples (due to sample quality), were stored at −70° C. until shipment to the Sponsor for possible future analysis or discard after report finalization.

c) Blood Culture

Blood was collected from an appropriate vein for hemoculture (targeted volumes of 1 mL during study or 10 mL at euthanasia) when febrile neutropenia was identified (absolute neutrophil count<$0.5 \times 10^9$/L, rectal temperature≥104° F./40.0° C.) and at euthanasia; however, animals were not sampled more than twice weekly (excluding at euthanasia). When sepsis was suspected by the Clinical Veterinarian based on clinical signs and physical examination on other days, blood collections and hemoculture were also performed.

Blood samples were inoculated directly from the syringe in which they were collected into vials for hemoculture. The volume of the blood sample determined from the graduations on the syringe was recorded. Inoculated blood vials were stored at room temperature and shipped to IDEXX as soon as possible after collection with reception at IDEXX within 3 days. Each sample was labeled with the animal number, date of collection, specimen type, storage conditions, blood volume and study number. Aerobic and anaerobic cultures were performed by IDEXX. Blood cultures that were positive for bacteria were subject to antibiotic sensitivity evaluation.

For hemoculture performed non-terminally, a blood sample (target volume of 1 mL) was collected from the cephalic vein (or another appropriate vessel). For hemoculture performed terminally, a blood sample (target volume of 10 mL) was collected from a femoral vein (or another appropriate vessel). For scheduled and unscheduled euthanasia, the skin was shaved and aseptically prepared with chlorhexidine gluconate 4% and alcohol 70%. The sample was collected using aseptic procedures and was transferred to culture media at IDEXX. Aerobic and anaerobic cultures were performed by IDEXX in accordance with their procedures.

Pharmacokinetics (PK)

Blood samples (a target of 1.0 mL each) were collected for romiplostim serum level determination from all animals for procedural uniformity as described below with exact times of each collection documented and provided to SRI International for the subsequent pharmacokinetic analysis. Subsequent analysis of romiplostim serum levels was performed on samples collected from animals that received romiplostim. Representative samples were analyzed as reference controls from animals in Groups 1 and 4 which only received reference item/vehicle or pegfilgrastim, respectively.

Pre-Irradiation (Day −2)

Day 1: pre- and 1, 2, 4, 8, and 12 hours post injection for all groups

Day 2 (24±1 hour after Day 1 dosing)

Day 3 (48±1 hour after Day 1 dosing)

Day 4 (72±1 hour after Day 1 dosing)

Day 8 (pre-injection and 1, 2, 4, 8, and 12 hours post injection in all groups)

Day 9 (24±1 hour after Day 8 dosing)

Day 10 (48±1 hour after Day 8 dosing)

Day 11 (72±1 hour after Day 8 dosing)

Approximately weekly thereafter (Day 14, 21, 28, and 35)

Day 45

Blood samples for PK were collected by femoral (except between Day 6 and 24), cephalic or saphenous vein. Serum separator tubes (SST) were filled with the appropriate amount of blood, gently inverted 5 times and allowed to clot for 30-60 minutes at room temperature. Samples were then centrifuged (set at 4° C., 1500 g) for a targeted 15 minutes. Serum was removed and aliquoted into 2 cryovials, placed on dry ice and transferred to a freezer set at −70° C. within 2 hours of blood collection. Serum samples were shipped weekly, on dry ice to Raquica Butler at Syneos Health for analysis. Aliquots from the same sample were not shipped in the same shipment. Samples were stored in a freezer set to maintain −60° C. or colder.

Serum samples were analyzed for concentration of romiplostim by Syneos Health using their validated sandwich immunoassay analytical method. Analysis of pre-irradiation (Day −2) samples was not performed because analysis of the Day 1 pre-injection samples was sufficient to show that romiplostim was absent from each of the animals prior to injection on Day 1.

Samples from Groups 1 and 4 were analyzed only at the following time points and served as representative, reference control samples:

Day 1: 4 hour post-injection

Day 2: 24 hour post-injection

Day 8: 4 hour post-injection

Group 1 samples from other time points (not listed above) on Days 1 and 8 were used for bioanalytical method post-irradiation selectivity testing.

A portion of the pharmacokinetic samples were re-analyzed for evaluation of the reproducibility of the bioanalytical method (incurred sample re-analysis). The incurred sample re-analysis values were not used for pharmacokinetic analysis.

The serum drug level data was analyzed using Phoenix® WinNonlin® software version 6.3 to perform non-compartmental modeling. The dose administered was input to the program as mg/kg, and as a result, no additional corrections for individual body weights of the animals were necessary.

The parameters and constants determined using non-compartmental analysis, when data allowed, included maximal serum concentration ($C_{max}$), time to maximum serum concentration ($T_{max}$), area under the serum concentration-time curve (AUC), and terminal elimination half-life ($t_{1/2}$).

Data Handling and Reporting

Data Capture

This study collected data commencing at least two weeks prior to the start of dosing. Data from one week prior to the start of dosing is considered adequate for baseline comparison. Any data that may have been collected prior to this period were maintained in the study file.

The following data capture systems were used during the conduct of this study.

In-life Data Collection: Provantis In-Life Module 9.3.0.0

Clinical Pathology: Provantis Clinical Pathology Module 9.3.0.0

Pathology: Provantis Pathology Module 9.3.0.0

Analytical: EZChrom Elite 3.3.1

Bioanalytical: Softmax Pro 5.2

Pharmacokinetics: Phoenix® WinNonlin 6.3

Statistical Analysis: SAS 9.2 and 9.3

Room Environment: Siemens Insight 3.13

Data Analysis

Data recorded on unscheduled occasions were reported on an individual basis, but not included in the following analysis.

Numerical data obtained during the conduct of the study were subjected to calculation of group means, median and standard deviations and reported. Non-numerical data obtained during the conduct of the study were reported as individual results and/or as group incidences.

Each pairwise group comparison of interest was conducted via a two-sided test at the 5% significance level and the significant results reported as either p≤0.001, p≤0.01 or p≤0.05, where p represents the observed probability.

Survival Data

The statistical group comparison of mortality data was performed on pooled sexes using Fisher's exact test and including all groups. The overall group comparison indicated significant differences in mortality rates (p≤0.05). The mortality rate of Group 1 was compared to each of the other groups using the Fisher's exact test. Since there was no mortality other than in Group 1, the Fisher's exact test could not be performed for the other pairwise group comparisons of interest.

Numerical Data

Plots of the treatment means [±standard error of the mean (SEM)] and medians across time were presented for males, females and pooled genders for absolute values of body weight, body weight change, body temperature, hematology parameters [white blood cell (WBC), neutrophil (NEUT), lymphocyte (LYMPH), monocyte (MONO), platelet (PLT), hematocrit, red blood cell (RBC) and reticulocyte (RETIC)].

Numerical Data Sets Submitted for Statistical Group Comparison:

Body weight and body weight change

Body temperature

Clinical pathology (hematology; all parameters including WBC, NEUT, LYMPH, PLT, RBC, RETIC, coagulation; on activated partial thromboplastin time, prothrombin time, fibrinogen)

The following statistical group comparison was performed by occasion in two phases for the numerical data sets listed above. The first phase assessed the romiplostim treatment effect alone. The second phase assessed the treatment effect of romiplostim, pegfilgrastim and their possible interaction.

Phase 1 Comparisons

The following statistical comparisons were used to assess the romiplostim treatment effect and included only results from Groups 1, 2, 3 and 5.

A univariate two-way analysis of variance (ANOVA) was performed for each occasion. The model included the Group, the Sex and the interaction Group*Sex as fixed effects.

To assess the significance of variance heterogeneity among the levels of the considered fixed effects, three heteroscedastic ANOVA models were fitted, respectively by modeling different covariance matrices for each level of 1—Group, 2—Sex, and 3—Group and Sex combination. When the final Hessian was not a positive definite for a model, or when computational limitation/convergence problems were encountered when fitting a model, the model results were not considered in the following steps. Among the successfully fitted heteroscedastic models, the one having the lowest corrected Akaike's Information Criterion (AICC) was selected and compared to the reduced homoscedastic ANOVA model (a model with a common covariance matrix for all levels of Group and Sex).

In order to test that the selected heteroscedastic model (the full model) provided a significantly better fit than the homoscedastic model (the reduced model), a likelihood ratio test based on REML estimation results was used. The results from the reduced model were retained when the likelihood ratio test was not significant (p>0.05). Otherwise, the full model results were retained. The Kenward and Roger's method was used to compute the denominator degrees of freedom for the tests involving the fixed effects. The alternative Satterthwaite method was used when the Kenward and Roger's method was not applicable.

When the retained model indicated that the fixed effects interaction was not significant from the retained ANOVA model (p>0.10), the group effect was assessed on least squares means pooled across sexes using the ANOVA F-test. When the interaction was significant (p≤0.10), the group effect was assessed for each Sex using the ANOVA F-test on least-squares means.

When the group effect was significant (p≤0.05), the pairwise comparisons of interest were performed using t-test on least-squares means. The pairwise comparisons of interest were the vehicle control Group 1 with each of the other groups and the Group 3 with Group 5.

Phase 2 Comparisons

The following statistical comparisons were used to assess the treatment effect of the romiplostim, the pegfilgrastim and their possible interaction and so, it was performed including only results from Groups 1, 3, 4 and 6.

A three-way analysis of variance (ANOVA) was performed. The model included the fixed effects romiplostim (2 levels: 0 and 5 mg/kg Day 1), pegfilgrastim (2 levels: 0 and 0.3 mg/kg Days 1 and 8), sex and their two-way and three-way interactions.

To assess the significance of variance heterogeneity among the levels of the considered fixed effects, heteroscedastic ANOVA models were fit, modeling different covariance matrices for each level of each fixed effect and for each level of fixed effect combination. When the final Hessian was not positive definite for a model or computational limitation/convergence problems were encountered when fitting a model, the model results were considered in the following steps. Among the considered heteroscedastic models, the one having the lowest corrected Akaike's Information Criterion (AICC) was selected and compared to the reduced homoscedastic ANOVA model (a model with a common covariance matrix for all levels of each fixed effect).

In order to test that the selected heteroscedastic model (the full model) provided a significantly better fit than the homoscedastic model (the reduced model), a likelihood ratio test based on REML estimation results was used. The results from the reduced model were retained when the likelihood ratio test was not significant (p>0.05). Otherwise, the full model results were retained. The Kenward and Roger's method was used to compute the denominator degrees of freedom for the tests involving the fixed effects. The alternative Satterthwaite method was used when the Kenward and Roger's method was not applicable.

When the retained three-way ANOVA indicated that the triple interaction was significant (p≤0.10), the romiplostim effect was assessed within each combination of pegfilgrastim and Sex and the pegfilgrastim effect was assessed within each combination of romiplostim and Sex using t-test on least-squares means.

Where there was no significant triple interaction (p>0.10), then the table below (Table 4) detailed how the romiplostim and pegfilgrastim effects were assessed depending on which interactions were significant (p≤0.10).

TABLE 4

| Romiplostim and Pegfilgrastim Interactions | | | | |
|---|---|---|---|---|
| Significant Interactions (p ≤ 0.10) | | | Effect Assessed | |
| romiplostim by pegfilgrastim | romiplostim by Sex | pegfilgrastim by Sex | romiplostim | pegfilgrastim |
| Yes | Yes | Yes | within each level of pegfilgrastim and sex | within each level of romiplostim and sex |
| Yes | Yes | No | within each level of pegfilgrastim and sex | within each level of romiplostim, sexes combined |
| Yes | No | Yes | within each level of pegfilgrastim, sexes combined | within each level of romiplostim and sex |

TABLE 4-continued

| Romiplostim and Pegfilgrastim Interactions | | | | |
|---|---|---|---|---|
| Significant Interactions (p ≤ 0.10) | | | | |
| romiplostim | romiplostim | pegfilgrastim | Effect Assessed | |
| by pegfilgrastim | by Sex | by Sex | romiplostim | pegfilgrastim |
| Yes | No | No | within each level of pegfilgrastim, sexes combined | within each level of romiplostim, sexes combined |
| No | Yes | Yes | within each level of Sex, pegfilgrastim combined | within each level of sex, romiplostim combined |
| No | Yes | No | within each level of Sex, pegfilgrastim combined | levels of romiplostim and sexes combined |
| No | No | Yes | levels of pegfilgrastim and sexes combined | within each level of sex, romiplostim combined |
| No | No | No | levels of pegfilgrastim and sexes combined | levels of romiplostim and sexes combined |

The assessment of the effects romiplostim and pegfilgrastim as described in the table above was performed using the t-test on the respective least-squares means from the ANOVA model. The significance of the romiplostim and pegfilgrastim effects were assessed at the 5% alpha level.

Results

Analysis of Test Item Concentration

The absence of test item concentration (romiplostim) in vehicle samples (Group 1, 2, 4) was demonstrated. Agreement with nominal concentration of the test item was inside a ±10% range from nominal (from −7.4 to −0.2% from nominal), as detailed in the following table:

TABLE 5

| | | Romiplostim Concentration | | |
|---|---|---|---|---|
| Groups | Nominal Concentration | Occasion | Measured Concentration (mg/mL) | % RE |
| 1, 2, 4 | Vehicle | Day 1, Rep A | BLQ | N/A |
| | 0 mg/mL | Day 1, Rep B | BLQ | N/A |
| | romiplostim | Day 1, Rep C | BLQ | N/A |
| | (0.9% NaCl | Day 8, Rep A | BLQ | N/A |
| | for injection) | Day 8, Rep B | BLQ | N/A |
| | | Day 8, Rep C | BLQ | N/A |
| 2, 3, 5, 6 | 0.5 mg/mL | Day 1, Rep A | 0.499 | −0.2 |
| | romiplostim | Day 1, Rep B | 0.469 | −6.3 |
| | | Day 1, Rep C | 0.469 | −6.3 |
| 5 | 0.5 mg/mL | Day 8, Rep A | 0.489 | −2.3 |
| | romiplostim | Day 8, Rep B | 0.483 | −3.3 |
| | | Day 8, Rep C | 0.463 | −7.4 |

BLQ: Below Limit of Quantification for Nplate (LOQ = 50.0 µL/mL);
N/A: Not applicable Mortality There were 6 mortalities during the conduct of the study (3 males and 3 females), all from Group 1 (vehicle). FIGS. 6A-6C present the survival curves (per sex, and sexes combined); indicating the irradiation level was approximately an $LD_{60/45}$ for this study.

Decreased appetence, hunched back, signs of hemorrhage (petechia) and diarrhea were seen in the groups (both genders) post-irradiation.

Decreased appetence was noted in all groups, with generally no difference between groups in incidence or severity. Diarrhea (liquid feces) was noted between Day 2 to 17, during the expected period of irradiation-induced diarrhea.

Hunched back was seen in all groups, with the highest incidence noted in Group 1. Males appeared to be less affected (with only one Group 3 male with this observation on 1 day) than females. Petechia was noted across all groups, with a slightly lower incidence in Group 6 animals.

The 3 animals that had hemocultures due to suspected febrile neutropenia (absolute neutrophil count<0.5× $10^9$/L; ≥40° C.) had negative results.

Other clinical signs (including, but not limited to skin wounds with or without discharge, fur thin, red liquid material, red discharge from vulva) were considered related to the experimental procedure (prophylactic subcutaneous injection of formulation, which potentially creates abscesses and wounds; thin fur due to shaving of the sites for dosimeter placement or blood collection sites) or seen in laboratory-housed members that are in estrus, and/or showed no relationship to dose levels in incidence or severity.

Hematology (Pharmacodynamics)

RBC (red blood cell) and HCT (hematocrit) values decreased post-irradiation, with all treated groups starting to recover by Day 17. Group 6 remained slightly higher, while Group 4 remained slightly lower, compared to the other treated groups.

RETIC (reticulocyte) levels all decreased post-irradiation, with no difference between the groups, including the control group. RETIC count recovery was improved in treated groups (i.e. romiplostim and/or pegfilgrastim) when compared to control but without significant differences between treatments.

WBC (white blood cell), LYMPH (lymphocyte) and MONO (monocyte) values decreased post-irradiation with gradual recovery starting around Day 17. For LYMPH, all treated groups (i.e. Groups 2 to 6) presented higher counts compared to Group 1 and were generally comparable to each other. For WBC and MONO, all treated groups had earlier recovery (with Group 6 having the earliest recovery), with higher counts compared to Group 1.

NEUT (neutrophil) levels decreased post-irradiation; Group 1 had its nadir on Day 14 ($0.13 \times 10^9$/L) with a start in recovery on Day 15 ($0.15 \times 10^9$/L), however Groups 4 and 6 were noted to have the least severe nadirs at $0.43 \times 10^9$/L and $0.56 \times 10^9$/L, respectively, compared to nadirs ranging from 0.09 to $0.13 \times 10^9$/L for the other groups. Nadirs for Groups 4 and 6 were significantly different only from Groups 1 and 3 (p≤0.05). The earliest recovery was noted on Day 13 for Group 6 (pegfilgrastim and romiplostim) with higher cell count ($1.25 \times 10^9$/L), followed by Group 4 (pegfilgrastim) on Day 13 with $0.51 \times 10^9$/L. Interestingly, Group 4 and 6 were also noted to present a transient rise in NEUT from Day 8 to 9, prior to the nadir. Although the animals in Group 5 were dosed twice with romiplostim, when compared to Group 3 (romiplostim administered once), no significant difference was observed for neutrophil count at nadir or start of recovery. FIG. 7 presents the median neutrophil counts (genders combined) and Table 7 shows the nadir and recovery days for neutrophils in each group (genders combined).

TABLE 7

Nadir and Recovery Days for Neutrophils (Genders Combined)

| Group | Nadir NEUT | Recovery NEUT |
|---|---|---|
| 1 | Day 14 ($0.13 \times 10^9$/L) | Day 15 ($0.15 \times 10^9$/L) |
| 2 | Day 14 ($0.12 \times 10^9$/L) | Day 15 ($0.14 \times 10^9$/L) |
| 3 | Day 14 ($0.12 \times 10^9$/L) | Day 15 ($0.30 \times 10^9$/L) |
| 4 | Day 12 ($0.43 \times 10^9$/L)[AB] | Day 13 ($0.51 \times 10^9$/L)[AB] |
| 5 | Day 13 ($0.09 \times 10^9$/L) | Day 14 ($0.12 \times 10^9$/L) |
| 6 | Day 11 ($0.56 \times 10^9$/L)[AB] | Day 13 ($1.25 \times 10^9$/L)[AB] |

[A]Statistically different from Group 1.
[B]Statistically different from Group 3.
[C]Statistically different from Group 4.

A: Statistically different from Group 1. B: Statistically different from Group 3. C: Statistically different from Group 4.

Severe thrombocytopenia was observed post-irradiation, with a PLT nadir of $20.6 \times 10^9$/L, 14 days post-irradiation in Group 1. Groups dosed with either romiplostim or pegfilgrastim (i.e. Groups 2 to 5) had less severe thrombocytopenia, with nadirs on Day 13, ranging from 47.6 to $71.0 \times 10^9$/L, while the group dosed with both romiplostim and pegfilgrastim (i.e. Group 6) presented the least severe nadir in platelet counts (at $92.1 \times 10^9$/L) on Day 11, significantly different ($p \leq 0.01$) compared to Groups 1 and 4. Group 6 also showed subsequent earlier recovery with higher PLT counts ($105.5 \times 10^9$/L, Day 12), compared to other groups. At nadir, the cell count observed for Group 3 (romiplostim administered once) and Group 5 (romiplostim administered twice) was very alike ($71 \times 10^9$/L and $69.1 \times 10^9$/L, respectively) and only significantly different from Group 1 ($p \leq 0.05$). A similar profile was noted at start of recovery for Group 3 and 5 ($81.8 \times 10^9$/L and $74.1 \times 10^9$/L, respectively). No significant difference was observed between Group 3 and Group 5. FIG. 8 presents the median platelet counts (genders combined), while Table 8 presents the platelet nadir and recovery (genders combined).

TABLE 8

Platelet Nadir and Recovery Days

| Group | Nadir PLT | Recovery PLT |
|---|---|---|
| 1 | Day 14 ($20.6 \times 10^9$/L) | Day 15 ($24 \times 10^9$/L) |
| 2 | Day 13 ($63 \times 10^9$/L)[A] | Day 14 ($64.6 \times 10^9$/L)[A] |
| 3 | Day 13 ($71 \times 10^9$/L)[A] | Day 14 ($81.8 \times 10^9$/L)[AC] |
| 4 | Day 13 ($47.6 \times 10^9$/L) | Day 14 ($63.5 \times 10^9$/L)[AB] |
| 5 | Day 13 ($69.1 \times 10^9$/L)[A] | Day 14 ($74.1 \times 10^9$/L) |
| 6 | Day 11 ($92.1 \times 10^9$/L)[AC] | Day 12 ($105.5 \times 10^9$/L)[AC] |

[A]Statistically different from Group 1.
[B]Statistically different from Group 3.
[C]Statistically different from Group 4.

During the remaining of the observation period, there were some fluctuations, however, all groups were comparable to baseline values by Day 45 There appeared to be a synergistic effect on neutrophil and platelet recovery when both romiplostim and pegfilgrastim were administered There were no changes seen in PT or aPTT during the study. There were some increases in individual results on occasion, however there were no correlating changes in the other coagulation parameters, and the increases may have been due to sample collection and handling, rather than a biological change.

Coagulation

Neither the administration of romiplostim or pegfilgrastim or combination thereof had any effects on secondary coagulation endpoints as there was no statistically significant treatment related differences in prothrombin time (PT) and activated partial thromboplastin time (aPTT) in treated compared with control groups. Fibrinogen levels increased slightly in all groups (including control) and were significantly greater in groups receiving pegfilgrastim (i.e. Groups 4 and 6) compared with control ($p < 0.05$) on Day 3. Values returned to baseline by Day 8 followed by a second rise which peaked between Days 14 and 17. Vehicle-treated animals (Group 1) presented the highest fibrinogen level with peak values on Day 17 suggesting greater inflammation in this group.

Pharmacokinetics

Table 9 shows the pharmacokinetics of romiplostim in the rhesus macaques. The mean (+/−standard error) of select pharmacokinetic parameters are shown. $C_{max}$: maximum serum concentration; $T_{max}$: time of maximum serum concentration; AUC: area under the curve/exposure; $T_{1/2}$: elimination half-life. RP: romiplostim; PF: pegfilgrastim. (Group 1, n=10; Groups 2-6, n=8).

TABLE 9

Pharmacokinetics of Romiplostim in Rhesus Macaques

| Group | Day of Dosing | $C_{max}$ (ng/ml) | $T_{max}$ (hr) | AUC (hr*ng/ml) | $T_{1/2}$ (hr) |
|---|---|---|---|---|---|
| 2 RP 2.5 mg/kg | 1 | 1207 (±263) | 7.0 (±0.7) | 31824 (±5588) | 45.0 (±6.6) |
| 3 RP 5.0 mg/kg | 1 | 2022 (±536) | 10 (±2.0) | 60108 (±13456) | 62.0 (±7.5) |
| 5 RP 5.0 mg/kg | 1 | 3265 (±457) | 8.0 (±0.5) | 68927 (±9965) | — |
| 5 RP 5.0 mg/kg | 8 | 4163 (±422) | 8.0 (±1.0) | 72853 (±12055) | 58.0 (±6.7) |
| 6 RP 5.0 mg/kg + PF 0.3 mg/kg | 1 | 2588 (±392) | 7.0 (±0.7) | 74692 (±7851) | 68.0 (±8.2) |

There was considerable variability in serum romiplostim concentrations between animals in several treatment groups, causing substantial variability in the resulting PK parameters.

Romiplostim was absorbed with a mean $T_{max}$ of ~5 to 12 hr after single dose administration in Groups 2, 3, and 6. romiplostim was eliminated with a mean terminal $t_{1/2}$ of ~37 to 74 hr after single dose administration in Groups 2, 3, and 6 and ~52 to 63 hr after the second dose in Group 5.

Serum romiplostim exposure increased disproportionately with a dose increment from 2.5 mg/kg (Group 2) to 5 mg/kg (Group 3). Mean $C_{max}$ and $AUC_{last}$ at 5 mg/kg (Group 3) were ~2.3- and 2.5-fold greater in males and 1.3- and 1.4-fold greater in females, respectively, than those determined at 2.5 mg/kg (Group 2) for a 2-fold dose increment from 2.5 to 5 mg/kg. Mean $C_{max}$ was 990±402 ng/ml (males) and 1,425±1,001 ng/ml (females) at 2.5 mg/kg (Group 2) and 2,263±1,790 ng/ml (males) and 1,782±1,421 ng/ml (females) at 5 mg/kg (Group 3). Corresponding mean $AUC_{last}$ was 30,147±11,164 hr*ng/ml (males) and 33,501±21,232 hr*ng/ml (females) at 2.5 mg/kg (Group 2) and 74,957±44,396 hr*ng/ml (males) and 45,260±28,652 hr*ng/ml (females) at 5.0 mg/kg (Group 3).

Serum romiplostim exposure was compared between the groups that were administered romiplostim at 5 mg/kg with and without co-administration of pegfilgrastim (Groups 3 and 6, respectively). The mean $C_{max}$ and $AUC_{last}$ decreased by ~15% in males and increased by over 80% in females with the addition of pegfilgrastim in Group 6, when compared with these parameters without pegfilgrastim in Group 3. In Group 6 with pegfilgrastim, the mean $C_{max}$ of romiplostim was 1,921±981 ng/ml (males) and 3,255±850 ng/ml (females) and the mean $AUC_{last}$ was 64,150±22,719 hr*ng/ml (males) and 85,233±18,387 hr*ng/ml (females). This suggests a greater exposure (>80%) of romiplostim when co-administered with pegfilgrastim in females. Females in Group 3 also had a lower romiplostim serum exposure by 21% ($C_{max}$) and ~40% ($AUC_{last}$) than males; hence, this could have contributed to the large difference observed in females in serum exposure between addition and no addition of pegfilgrastim in the dose regimen (i.e., Group 6 vs. Group 3).

Regarding two administrations of romiplostim (Day 1 and Day 8, Group 5), the overall mean $T_{max}$ was 8.0 hr in two animals and 180.0 and 176.0 hr in the other two animals in males and 176.0±3.3 hr in females. The overall mean $C_{max}$ after administration of both doses was 3,800±1,616 ng/ml (males) and 4,778±467 ng/ml (females); and the overall mean $AUC_{last}$ was 153,103±53,375 hr*ng/ml (males) and 180,394±33,936 hr*ng/ml (females). For the individual doses, the mean $C_{max (Dose\ 1)}$ was 3,186±1,951 ng/ml (males) and 3,345±291 ng/ml (females) and the mean $C_{max\ (Dose\ 2)}$ was 3,548±1,448 ng/ml (males) and 4,778±467 ng/ml (females). The mean $AUC_{(0-72\ hr,\ Dose\ 1)}$ was 71,789±41,898 hr*ng/ml (males) and 66,065±8,732 hr*ng/ml (females) and the mean $AUC_{(0-72\ hr,\ Dose\ 2)}$ was 55,593±36,237 hr*ng/ml (males) and 90,113±24,604 hr*ng/ml (females). There was a trend toward accumulation of romiplostim with repeat administration that was more evident in females. The mean $C_{max}$ and $AUC_{(0-72\ hr)}$ were ~43% and ~36% greater in females after administration of Dose 2 when compared with Dose 1, respectively. In males, the $C_{max}$ and $AUC_{(0-72\ hr)}$ were ~11% greater and ~23% lower, respectively, after administration of Dose 2 when compared with Dose 1. However, the variability in serum romiplostim concentrations in Group 5 was more prominent in males than in females. Measurable serum concentrations of romiplostim were noted prior to Dose 2 administration in most animals in Group 5 and may have contributed to the greater serum exposure after Dose 2 in this group, notably in females.

Discussion

Subcutaneous administration of romiplostim (at varying dose levels or occasions), pegfilgrastim or a combination of both romiplostim and pegfilgrastim, following total-body irradiation at 550 cGy, resulted in a 60% mortality in control animals with no mortalities observed in any of the romiplostim or pegfilgrastim groups.

Clinical signs, body weight changes, body temperature changes expected in the radiation model were of lesser severity and/or incidence in the treated groups, with Group 6 showing earlier recovery and higher body weights compared to the other treated groups. There were no changes in the coagulation parameters.

Hematology parameters (RBC, HCT, WBC, LYMPH, MONO) had expected decreases post-irradiation, with all treated groups showing earlier and improved recovery, compared to the control group (FIGS. 11A-11E). Generally, Group 6 (dosed with both romiplostim and pegfilgrastim) was noted to have earlier recovery with higher results compared to the other treated groups. NEUT and PLT levels decreased as expected post-irradiation. Group 4 and 6 (both dosed with pegfilgrastim), showed earlier recovery compared to the rest of the treated groups (as expected, as pegfilgrastim stimulates myeloid lineages), however Group 6 (dosed with both romiplostim and pegfilgrastim) was noted to have earlier recovery on Day 13 with higher cell count ($1.25 \times 10^9$/L) compared to Group 4 (pegfilgrastim alone) with $0.51 \times 10^9$/L for NEUT. PLT nadirs were less severe in the treated groups; however, the group with the least severe PLT nadirs and earliest recovery was Group 6 (dosed with both romiplostim and pegfilgrastim) with cell counts at $92.1 \times 10^9$/L (nadir on Day 11) and $105.5 \times 10^9$/L (start of recovery on Day 12), significantly different ($p \leq 0.01$) from Groups 1 and 4. Although the animals in Group 5 were dosed twice with romiplostim, when compared to Group 3 (romiplostim administered once), no significant difference was observed for neutrophil or platelet counts at nadir or start of recovery.

There appeared to be a greater effect on neutrophil and platelet recovery when both romiplostim and pegfilgrastim were administered than when either agent was administered alone.

Considerable variability between animals within treatment groups was observed in serum romiplostim concentrations that resulted in substantial variability in PK parameters. The serum exposure of romiplostim, based on mean $C_{max}$ and $AUC_{last}$ values, increased by over 80% in females and decreased by ~15% in males when co-administered with pegfilgrastim, suggesting that pegfilgrastim influenced the pharmacokinetics of romiplostim, and this effect was more prominent in females. A dose increment from 2.5 to 5 mg/kg, when administered by itself, resulted in disproportionate changes in serum exposure of romiplostim. There was a trend toward accumulation of romiplostim with repeat administration, that was also more evident in females, as ~43% greater mean $C_{max}$ and ~36% greater $AUC_{(0-72\ hr)}$ were determined in females after administration of Dose 2 when compared with Dose 1.

The NHP effects of romiplostim presented here are in accordance with the studies of romiplostim administered in irradiated mice reported herein and also earlier studies that demonstrated that thrombopoietin (TPO) administration improves platelet levels and survival in irradiated NHPs (Neelis et al. (1997), Blood 90(7):2565-2573; Neelis et al.

(1997), *Exp Hematol.* 25(10):1084-1093). As with the NHP study reported herein, a single dose of TPO was as efficient as repeat doses to mitigate thrombocytopenia. However, neutralizing antibodies develop after TPO administration and investigation into its use has largely been abandoned. Romiplostim acts as a TPO receptor agonist, but with no sequence homology to TPO, hence with considerably lower risk for neutralizing antibodies to develop.

In addition to anticipated effects on neutrophil counts, pegfilgrastim also appeared to improve platelet counts, a finding that has been reported previously (Hankey et al. (2015), *Radiat Res.* 183(6):643-655). However, the results reported herein indicate that romiplostim is more potent in the treatment of radiation induced thrombocytopenia than pegfilgrastim alone.

The combination of both romiplostim and pegfilgrastim improved platelet and neutrophil counts to levels above those observed with either agent administered alone. These results suggest that these two agents, though presumably acting on different hematopoietic pathways and lineages, have beneficial effects on both neutrophil and platelet generation. This finding is important, as an inverse correlation between the number of days with severe thrombocytopenia and neutropenia and survival was reported in irradiated rhesus macaques (Stickney et al. (2007), *Int Immunophar-macol.* 7(4):500-505). Increased effectiveness in ARS has been observed with the administration of TPO and G-CSF to irradiated rhesus macaques (Neelis et al. (1997), *Blood* 90(7):2565-2573; Neelis et al. (1997), *Exp Hematol.* 25(10): 1084-1093) and mice (Grossmann et al. (1996) *Blood,* 88(9):3363-3370). In those studies, the apparent increase in neutrophil response to G-CSF was attributed to TPO-mediated bone marrow progenitor cell expansion, including granulocyte/monocyte colony forming units (GM-CFU) (Farese et al. (1996), *J Clin Invest.* 97(9):2145-2151; Ku et al. (1996), *Blood,* 87(11):4544-4551; Sitnicka et al. (1996), *Blood,* 87(12):4998-5005). Additionally, the effects of romiplostim and pegfilgrastim may be due to a complex interaction between TPO and G-CSF with effects on megakaryocytes and neutrophils. In mice, injection of G-CSF results in an increase in TPO levels in bone marrow and the release of neutrophil attracting cytokines from megakaryocytes and mobilization of neutrophils (Kohler et al. (2011), *Blood,* 117(16):4349-4357). The administration of pegfilgrastim may therefore also stimulate TPO production leading to increased thrombopoiesis while romiplostim (and TPO) may in turn stimulate the mobilization of neutrophils.

In addition to improved platelet levels, the inventors report for the first time that romiplostim and pegfilgrastim contribute to maintain the mean platelet volume (MPV)

above control levels after radiation (FIG. 8B), classically recognized as a marker for platelet activity and turnover (Thompson et al. (1984), *Blood,* 63(6):1372-1375). This is another indication that both these agents, especially in combination, stimulate thrombopoiesis with potential effects on the incidence of hemorrhages and ultimately improved survival outcomes. Decreased MPV has been associated with shorter survival in non-small lung cancer patients (Inagaki et al. (2014), *Lung Cancer,* 83(1):97-101; Kumagai et al. (2015), *Mol Clin Oncol.* 3(1):197-201).

Each reference cited in this specification is incorporated by reference in its entirety. It is understood that the disclosed invention is not limited to the particular methodology, protocols and materials described as these can vary. It is also understood that the terminology used herein is for the purposes of describing particular embodiments only and is not intended to limit the scope of the appended claims.

Those skilled in the art will recognize, or be able to ascertain using no more than routine experimentation, many equivalents to the specific embodiments of the invention described herein. Such equivalents are intended to be encompassed by the claims that follow.

What is claimed is:

1. A method of treating thrombocytopenia in a patient in need thereof, comprising co-administering romiplostim and pegfilgrastim to the patient, wherein romiplostim is administered at an initial dose of 1 mcg/kg once weekly, and adjusting weekly doses of romiplostim by increments of 1 mcg/kg to achieve and maintain a platelet count >50×10⁹/L, wherein the patient has been exposed to radiation, and wherein the pegfilgrastim is administered in two doses of 6 mg each one week apart.

2. The method of claim 1, wherein the patient has acute radiation syndrome.

3. The method of claim 1, wherein the patient has received or is receiving radiation therapy.

4. The method of claim 1, wherein the patient has received or is receiving chemotherapy.

5. A method of treating thrombocytopenia in a patient in need thereof, comprising co-administering romiplostim and pegfilgrastim to the patient, wherein romiplostim is administered at an initial dose of 1 mcg/kg once weekly, and adjusting weekly doses of romiplostim by increments of 1 mcg/kg to achieve and maintain a platelet count >50×10⁹/L, wherein the patient has idiopathic thrombocytopenia purpura or immune thrombocytopenia (ITP), and wherein the pegfilgrastim is administered in two doses of 6 mg each one week apart.

* * * * *